(12) United States Patent
Tang et al.

(10) Patent No.: US 9,024,001 B2
(45) Date of Patent: May 5, 2015

(54) ALPHAVIRUS REPLICON PACKAGING CONSTRUCTS

(75) Inventors: Zequn Tang, San Ramon, CA (US); Silvia Perri, Castro Valley, CA (US); John Polo, Danville, CA (US)

(73) Assignee: Novartis Vaccines and Diagnostics, Inc., Cambridge, MA (US)

( * ) Notice: Subject to any disclaimer, the term of this patent is extended or adjusted under 35 U.S.C. 154(b) by 1990 days.

(21) Appl. No.: 11/597,452

(22) PCT Filed: May 20, 2005

(86) PCT No.: PCT/US2005/017890
§ 371 (c)(1),
(2), (4) Date: Sep. 26, 2007

(87) PCT Pub. No.: WO2006/076032
PCT Pub. Date: Jul. 20, 2006

(65) Prior Publication Data
US 2008/0069804 A1 Mar. 20, 2008

Related U.S. Application Data

(60) Provisional application No. 60/574,025, filed on May 25, 2004.

(51) Int. Cl.
*C07H 21/00* (2006.01)
*A01N 63/00* (2006.01)
*C12N 7/00* (2006.01)
*C12N 1/02* (2006.01)
*C12N 15/00* (2006.01)
*C12N 15/86* (2006.01)

(52) U.S. Cl.
CPC ............ *C12N 15/86* (2013.01); *C12N 2510/00* (2013.01); *C12N 2770/36143* (2013.01)

(58) Field of Classification Search
CPC .............. C12N 2510/00; C12N 15/86; C12N 2770/36143; A61K 2039/5252; A61K 2039/5256; A61K 2039/5258; A61K 2039/53; A61K 2039/70; A61K 39/12; A61K 39/145; A61K 39/155; A61K 39/00; A61K 48/00

USPC ...................... 536/23.1; 435/239, 243, 320.1; 424/93.6
See application file for complete search history.

(56) References Cited

U.S. PATENT DOCUMENTS

| 5,091,309 | A | 2/1992 | Schlesinger et al. | |
| 6,426,196 | B1 * | 7/2002 | Dubensky et al. | 435/69.1 |
| 6,812,339 | B1 * | 11/2004 | Venter et al. | 536/24.31 |
| 2003/0119182 | A1 | 6/2003 | Smith et al. | |
| 2004/0235133 | A1 * | 11/2004 | Frolov et al. | 435/235.1 |

FOREIGN PATENT DOCUMENTS

WO 2006078294 7/2006

OTHER PUBLICATIONS

Bredenbeek et al. J. Virol 67:6439-6446, 1993.*
NCBI accession No. K00438, dated Jul. 10, 2001, pp. 1.*
NCBI accession No. K00444.1 , p. 1.*
Gorchakov, Rodion et al., "Selection of Functional 5' Cis-Acting Elements Promoting Efficient Sindbis Virus Genome Replication," Journal of Virology, vol. 78, No. 1, Jan. 2004, pp. 61-75.
Kuhn, R et al., "Attenuation of Sindbis Virus Neurovirulence by Using Defined Mutations in Nontranslated Regions of the Genome RNA," Journal of Virology, New York, US, vol. 66, No. 12, Dec. 1992, pp. 7121-7127.
Frolova et al., "Packaging Signals in Alphaviruses," Journal of Virology, The American Society for Microbiology, US, vol. 71, No. 1, Jan. 1997, pp. 248-258.
Baumstark T et al., "The Brome Mosiac Virus RNA3 Intergenic Replication Enhancer Folds to Mimic a tRNA TpsiC-Stem Loop and is Modified In Vivo," RNA, New York, NY, vol. 7, No. 11, Nov. 2001, pp. 1652-1670.
Fayzulin Rafik et al., "Changes of the Secondary Structure of the 5' End of the Sindbis Virus Genome Inhibit Virus Growth in Mosquito Cells and Lead to Accumulation of Adaptive Mutations," Journal of Virology, vol. 78, No. 10, May 2004, pp. 4953-4964.
Maruggi, Giulietta, et al., "Engineered alphavirus replicon vaccines based on known attenuated viral mutants show limited effects on immunogenicity," Virology, 2013, pp. 254-264, vol. 447.

* cited by examiner

*Primary Examiner* — Anoop Singh
(74) *Attorney, Agent, or Firm* — Laurence Shumway

(57) ABSTRACT

Provided herein are modified, functional 5' amplification sequences that are defective packaging signals. Also provided are compositions and methods comprising these modified 5' amplification sequences.

20 Claims, 5 Drawing Sheets

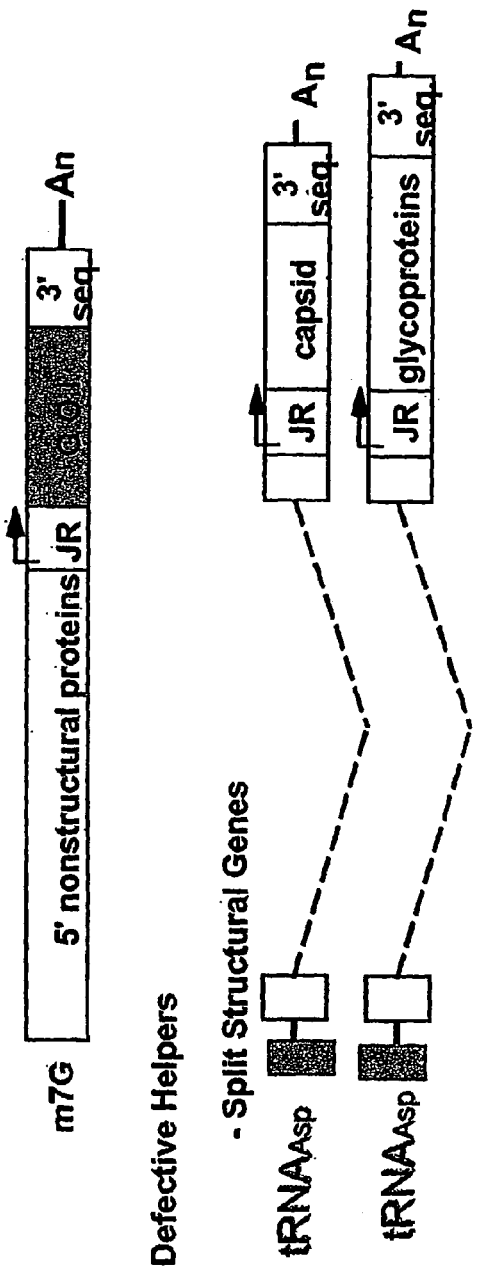

```
unmod:  ATGGATATAGTGGTGAGTATCCCCGCCTGTCACGCGGGAGACCGGGGTTCGGTTCCCCGACGGGGAGC  (SEQ ID NO:2)
mod#1:  ATGGATATAGTGGTGAGTATCCCCGCCTGTCACGCCTGTCACGCGGGACGGGGTTGTCGGGGACGGGGAGC  (SEQ ID NO:4)
mod#2:  ATGGATATAGTGGTGAGTATCCCCGCCTGTCACGCCTGTCACGCGGGGTTCAGCTGGGGGTTCGCGGACGGGGAGC  (SEQ ID NO:5)
mod#3:  ATGGATATAGTGGTGAGTATCCCCGCCTGTCACGCGCGGAGGTGCGGGTTGCACTCCGCGACGGGGAGC  (SEQ ID NO:6)
mod#4:  ATGGATATAGTGGTGAGTATCCCCGCCTGTCACGCCGGAGCAGCGGGTTGCTGTCCGACGGGGAGC  (SEQ ID NO:7)
mod#5:  ATGGATATAGTGGTGAGTATCCCCGCCTGTCACGGGCCAGGTCGGGGTTCGACTCGCCGACGGGGAGC  (SEQ ID NO:8)
mod#6:  ATGGATATAGTGGTGAGTATCCCCGCCTGTCACGCCCGAGGCTGGGGTTCAGCTCCGGGACGGGGAGC  (SEQ ID NO:9)
mod#7:  ATGGATATAGTGGTGAGTATCCCCGCCTGTCACGCCCGAGCCTCACGCCTCAGGTCAGGTTCAGGTCGGGGACGGGGAGC  (SEQ ID NO:10)
mod#8:  ATGGATATAGTGGTGAGTATCCCCGCCTGTCACGCCGGGGACGGGGTTGTCCTCGGGGACGGGGAGC  (SEQ ID NO:11)
mod#9:  ATGGATATAGTGGTGAGTATCCCCGCCTGTCACGCCCCAGGACCAGGGGTTCCTGTCGGGGACGGGGAGC  (SEQ ID NO:12)
mod#10: ATGGATATAGTGGTGAGTATCCCCGCCTGTCACGCCCCCAGCCAGGGGTTCTGGTCGGGGACGGGGAGC  (SEQ ID NO:13)
mod#11: ATGGATATAGTGGTGAGTATCCCCGCCTGTCACGCCCCCAGGGTCGGGTTGACCTCGGGGACGGGGAGC  (SEQ ID NO:14)
mod#12: ATGGATATAGTGGTGAGTATCCCCGCCTGTCACGCCCCCAGCCAGGGTTCGGGTTGACGTCGGGGACGGGGAGC  (SEQ ID NO:15)
mod#13: ATGGATATAGTGGTGAGTATCCCCGCCTGTCACGCCCCCAGGACGGGGTTCGTCTCGGGGACGGGGAGC  (SEQ ID NO:16)
```

FIGURE 3 tRNA secondary structures
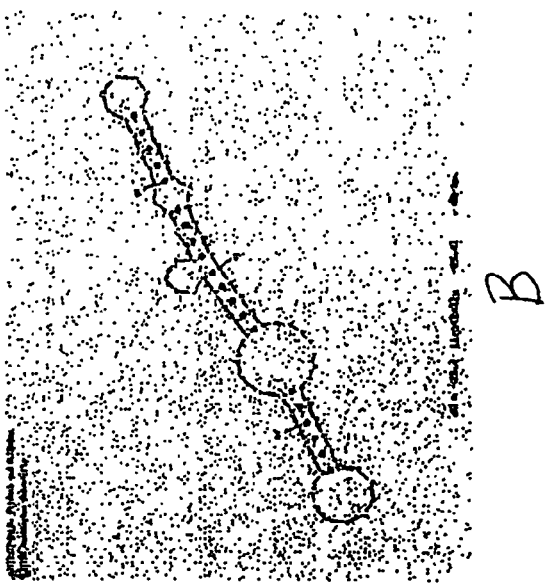
Modified tRNAasp
B
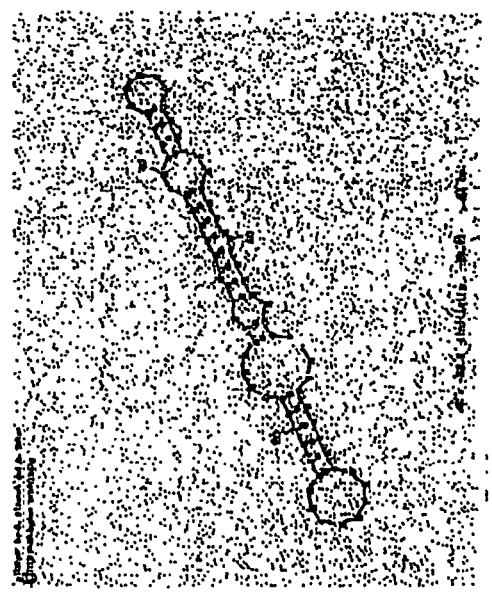
Wt tRNAasp
A
Fig. 4

ALPHAVIRUS REPLICON PACKAGING CONSTRUCTS

RELATED APPLICATIONS

This application is the U.S. National Phase of International Application No. PCT/US2005/017890, filed May 20, 2005 and published in English, which claims benefit to U.S. Provisional Application No. 60/574,025, filed May 25, 2004. The teachings of the above applications are incorporated herein in their entirety by reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 223002112200SEQLIST.txt, date recorded: Jun. 14, 2010, size: 5 KB).

TECHNICAL FIELD

The present invention relates generally to pharmaceutical compositions. In particular, the invention relates to modified cis-acting, functioning amplification sequences that are defective as packaging signals and to methods of making and using these sequences.

BACKGROUND

Alphaviruses comprise a set of genetically, structurally, and serologically related arthropod-borne viruses of the Togaviridae family. Twenty-six known viruses and virus subtypes have been classified within the alphavirus genus, including, Sindbis virus (SIN), Semliki Forest virus (SFV), Ross River virus (RRV), and Venezuelan equine encephalitis virus (VEE).

Several members of the alphavirus genus are being developed as "replicon" expression vectors for use as vaccines and therapeutics. Replicon vectors may be utilized in several formats, including DNA, RNA, and to make recombinant virus-like particles containing the replicon vectors (replicon particles). Such replicon vectors have been derived from alphaviruses that include, for example, SIN (Xiong et al. (1989) *Science* 243:1188-1191; Dubensky et al., (1996) *J. Virol.* 70:508-519; Hariharan et al. (1998) *J. Virol.* 72:950-958; Polo et al. (1999)*PNAS* 96:4598-4603), Semliki Forest virus (Liljestrom (1991) *Bio/Technology* 9:1356-1361; Berglund et al. (1998) *Nat. Biotech.* 16:562-565), and VEE (Pushko et al. (1997) *Virology* 239:389-401). A wide body of literature has now demonstrated efficacy of using alphavirus replicon vectors for applications such as vaccines (see for example, Dubensky et al., ibid; Berglund et al., ibid; Hariharan et al., ibid, Pushko et al., ibid; Polo et al., ibid; Davis et al. (2000) *J Virol.* 74:371-378; Schlesinger & Dubensky (1999) *Curr Opin. Biotechnol.* 10:434-439; Berglund et al. (1999) *Vaccine* 17:497-507).

The use of alphavirus replicon vectors as nucleic acid-based vaccines may provide certain advantages as compared to other nucleic acid expression vectors. Through the years, several terms including alphavirus vector, alphavirus vector construct, alphavirus replicon, alphavirus RNA replicon, alphavirus vector replicon, Eukaryotic Layered Vector Initiation System (ELVIS), alphavirus plasmid replicon and the like have emerged to describe alphavirus replicon vectors.

In addition to their use as gene delivery vehicles, alphavirus replicon vectors have also been described for use to generate recombinant viral or virus-like particles (replicon particles), which are themselves useful in prophylactic and therapeutic applications. See, e.g., Polo et al. (1999) *Proc Natl Acad Sci USA* 96(8):4598-4603. Alphavirus replicon particles are typically generated using a multi-component system that separates the various elements required for particle formation. Separation of the various elements reduces the risk of generating undesirable, replication-competent virus. The systems typically include: 1) a replicon vector, which contains elements necessary for its own intracellular replication (e.g., nonstructural protein coding sequences) but lacks one or more structural protein encoding elements needed for production of progeny particles, and 2) one or more structural protein expression cassette constructs (e.g., defective helpers) that encode alphavirus structural proteins (e.g., capsid, glycoproteins) required for packaging. The replicon constructs and the defective helper constructs can be introduced directly into cells as RNAs or launched from DNA in either transiently or stably transfected cells (e.g., packaging cell lines or PCL). See, e.g., Polo et al. (1999) *Proc. Nat'l Acad. Sci USA* 96:4598-4603; U.S. Pat. Nos. 6,465,634; 6,426,196; 6,376,236; 6,342,372; 6,015,686; and 5,843,723. Dubensky, T W et al. (1996) *J. Virology* 70(1):508-519; Frolov et al. (1996). *Proc Natl Acad Sci USA*. 93(21):11371-11377).

Ideally, the populations of alphavirus replicon particles used in prophylactic or therapeutic applications would be substantially homogenous and contain only the replicon RNA. However, even when the packaging elements are separated, particles containing additional RNA species (e.g., defective helper RNA) can occur. This undesirable packaging of non-replicon RNA species is also termed "co-packaging."

Thus, despite the advances in alphaviral vector technology, there remains a need for pharmaceutical compositions comprising and methods of making and using alphaviral vectors and alphavirus replicon particles, for example to reduce co-packaging.

SUMMARY

The present invention includes compositions comprising amplification sequences that are modified to be defective as packaging signals and methods of making and using these compositions.

In one aspect, the invention includes an isolated polynucleotide comprising a modified 5' amplification sequence, wherein the modified sequence provides a recognition site for synthesis of positive strand alphavirus RNA (from the complementary minus strand RNA intermediate) but does not provide a recognition site for RNA packaging. In certain embodiments, the modified 5' amplification sequence comprises a sequence that exhibits reduced homology (sequence identity) to packaging signals at the primary sequence level, while the secondary structure remains that of the original amplification sequence. In certain embodiments, the modified 5' amplification sequence is RNA. Furthermore, in certain embodiments, the modified 5' amplification sequence comprises any one of SEQ ID NOs:4-16 or a sequence exhibiting at least about 50% to about 60% (or any value therebetween, for example 50%, 51%, 52%, 53%, 54%, 55%, 56%, 57%, 58%, 59%, 60%) sequence identity to any of SEQ ID NOs:4 to 16, a sequence exhibiting at least about 60% to about 70% (or any value therebetween, for example 60%, 61%, 62%, 63%, 64%, 65%, 66%, 67%, 68%, 69%, 70%) sequence identity to any of SEQ ID NOs:4 to 16, a sequence exhibiting at least about 70% to about 80% (or any value therebetween, for example 70%, 71%, 72%, 73%, 74%, 75%, 76%, 77%, 78%, 79%, 80%) sequence identity to any of SEQ ID NOs:4 to 16, a sequence exhibiting at least about 80% to about 90% (or any value therebetween, for example 80%, 81%, 82%, 83%, 84%, 85%, 86%, 87%, 88%, 89%, 90%) sequence identity to any of SEQ ID NOs:4 to 16, or a sequence exhibiting at least about 90% to 99% (or any value therebetween, for example 90%, 91%, 92%, 93%, 94%, 95%, 96%, 97%, 98%, 99%) sequence identity to any of SEQ ID NOs:4 to 16.

In any of the modified 5' amplification sequences described herein, the sequence may be synthetic and/or may be derived from a sequence selected from the group consisting of a native alphavirus 5' sequence, a non-native DI alphavirus 5' sequence, a non-alphavirus derived viral sequence and a cellular RNA derived sequence, so long as the modified sequence provides a recognition site for synthesis of positive strand alphavirus RNA but does not provide a recognition site for RNA packaging. In certain embodiments, the modified 5' amplification sequence comprises a sequence exhibiting less than 90% identity a native alphavirus 5' sequence, a non-native DI alphavirus 5' sequence, a non-alphavirus derived viral sequence or a cellular RNA derived sequence. In other embodiments, the modified 5' amplification sequence comprises a sequence exhibiting less than 80% sequence identity to a native alphavirus 5' sequence, a non-native DI alphavirus 5' sequence, a non-alphavirus derived viral sequence or a cellular RNA derived sequence. In other embodiments, the modified 5' amplification sequence comprises a sequence exhibiting less than 70% sequence identity to a native alphavirus 5' sequence, a non-native DI alphavirus 5' sequence, a non-alphavirus derived viral sequence or a cellular RNA derived sequence. In still other embodiments, the modified 5' amplification sequence comprises a sequence exhibiting at least about 60% sequence identity to a native alphavirus 5' sequence, a non-native DI alphavirus 5' sequence, a non-alphavirus derived viral sequence or a cellular RNA derived sequence. In other embodiments, the modified 5' amplification sequence comprises a sequence exhibiting at least between about 40% and about 50% (or any value therebetween, for example 40%, 41%, 42%, 43%, 44%, 45%, 46%, 47%, 48%, 49%, 50%) sequence identity to a native alphavirus 5' sequence, a non-native DI alphavirus 5' sequence, a non-alphavirus derived viral sequence or a cellular RNA derived sequence. In still other embodiments, the modified 5' amplification sequence comprises a sequence exhibiting at least between about 30% and about 40% (or any value therebetween, for example 30%, 31%, 32%, 33%, 34%, 35%, 36%, 37%, 38%, 39%, 40%) sequence identity to a native alphavirus 5' sequence, a non-native DI alphavirus 5' sequence, a non-alphavirus derived viral sequence or a cellular RNA derived sequence. In still other embodiments, the modified 5' amplification sequence comprises a sequence exhibiting less than about 30% sequence identity to a native alphavirus 5' sequence, a non-native DI alphavirus 5' sequence, a non-alphavirus derived viral sequence or a cellular RNA derived sequence.

In another aspect, the invention comprises an RNA vector construct comprising any of the 5' amplification sequences described herein. In certain embodiments, the vector construct may further comprise a nucleic acid sequence encoding an alphavirus junction region promoter; a nucleic acid sequence encoding one or more alphavirus structural proteins (e.g., glycoproteins E1 and/or E2; capsid protein(s); etc.); and/or an RNA polymerase recognition sequence. Furthermore, the vector construct may also further comprise a nucleic acid sequence encoding a selectable marker. Any of the RNA vector constructs described herein may encode less than all biologically active alphavirus nonstructural proteins. Furthermore, any of the vector constructs described herein may include sequences derived from more than one alphavirus.

In another aspect, the invention includes an alphavirus vector construct comprising a 5' promoter operably linked to a nucleic acid molecule, wherein said nucleic acid molecule is complementary DNA to the RNA vectors described herein. In certain embodiments, the vector constructs may further comprise a 3' sequence that controls transcription termination. The 5' promoter may be a prokaryotic or a eukaryotic promoter.

In yet another aspect, the invention includes a cell comprising any of the alphavirus vector constructs described herein.

In yet another aspect, the invention includes an alphavirus packaging cell line, comprising a host cell and one or more of the alphavirus vectors described herein.

In a still further aspect, the invention includes a helper cell for producing an infectious, defective (replication defective) alphavirus particle, comprising in an alphavirus-permissive cell: an alphavirus replicon vector; and one or more separate expression cassettes (e.g., helper constructs) encoding the alphavirus structural protein(s) absent from the replicon vector, wherein at least one of said separate helper constructs comprise a modified 5' amplification sequence described herein and further wherein the combined expression of the replicon vector and the separate structural protein expression cassette(s) (e.g., helper vectors) produces an assembled alphavirus particle which comprises one or more heterologous sequence(s), is able to infect a cell, and is unable to complete viral replication. In certain embodiments, the helper cell comprises two separate structural protein expression cassette constructs (e.g., helper constructs), wherein a first structural protein expression cassette or helper construct encodes an alphavirus capsid protein and a second structural protein expression cassette or helper construct encodes alphavirus glycoproteins. One or more of the separate structural protein expression cassette or helper constructs may comprise a modified 5' amplification sequence. Preferably, the helper cell is transfected with the alphavirus replicon vectors and the one or more separate structural protein expression cassette helper constructs.

In another aspect, the invention includes a method of making infectious, defective (replication-defective), alphavirus particles, comprising: (a) providing a helper cell as described herein; (b) producing the alphavirus particles in the helper cell; and (c) collecting the alphavirus particles produced from the helper cell.

In another aspect, the invention includes a composition comprising infectious, replication-defective, alphavirus particles produced according to any of the methods described herein, wherein the composition is free from detectable replication-competent alphavirus particles.

In yet another aspect, the invention includes a pharmaceutical formulation comprising infectious, replication-defective, alphavirus particles produced by any of the methods described herein in a pharmaceutically acceptable carrier.

In a still further aspect, the invention includes a method of making any of the modified 5' amplification sequences described herein, the method comprising the steps of (a) determining regions of sequence homology between a known 5' amplification sequence and a sequence containing a viral packaging signal; and (b) altering the primary sequence of the known 5' amplification sequence such that the homology to the sequence containing a viral packaging signal is reduced but amplification function is retained, thereby making a modified 5' amplification sequence. In certain embodiments, the known 5' amplification sequence is selected from the group consisting of a native alphavirus 5' sequences, a non-native DI alphavirus 5'-end, a non-alphavirus derived viral sequence and a cellular RNA derived sequence.

These and other aspects and embodiments of the invention will become evident upon reference to the following detailed description and various references set forth herein that describe in more detail certain procedures or compositions (e.g., plasmids, sequences, etc.).

BRIEF DESCRIPTION OF THE DRAWINGS

FIG. 1 is a schematic depiction of a multiple construct system for generating alphavirus replicon particles. The replicon vector includes 5' and 3' end cis replication sequences, alphavirus non-structural genes, subgenomic junction region (JR) promoter and a heterologous gene of interest (GOI). The structural protein expression cassettes (defective helpers) depicted include a cis-acting tRNA-asparagine (tRNAasp or $tRNA_{Asp}$) 5' amplification sequence, a subgenomic junction region (JR) promoter, 3' end cis replication sequences and capsid- or glycoprotein-encoding sequences.

FIG. 2 depicts alignment of a portion of the putative Sindbis (SIN) packaging signal (SEQ ID NO:1) with a $tRNA_{Asp}$ 5' sequence (SEQ ID NO:2). The bottom line shows the consensus sequence (SEQ ID NO:3), and shows a region of high homology extending from about nucleotides 1029 to 1050 of a SIN genome (GenBank Accession No. NC001547).

FIG. 3 depicts alignment of an unmodified tRNA 5' sequence (SEQ ID NO:2) with various exemplary modified tRNA sequence (SEQ ID NOs: 4-16). Nucleotides that are altered with respect to a wild type tRNAasp sequence are underlined.

FIGS. 4A and 4B are schematic depictions of the secondary structure formed by unmodified and modified 5' amplification sequences. FIG. 4A shows the secondary structure of unmodified (wild type) tRNAasp (SEQ ID NO:2) and FIG. 4B shows the secondary structure of an exemplary modified 5' amplification sequence, termed mod #1 (SEQ ID NO:4).

FIG. 5A shows results at a multiplicity of infection 2 (MOI 2). FIG. 5B shows results at MOI 4.

DETAILED DESCRIPTION

Figure 5:
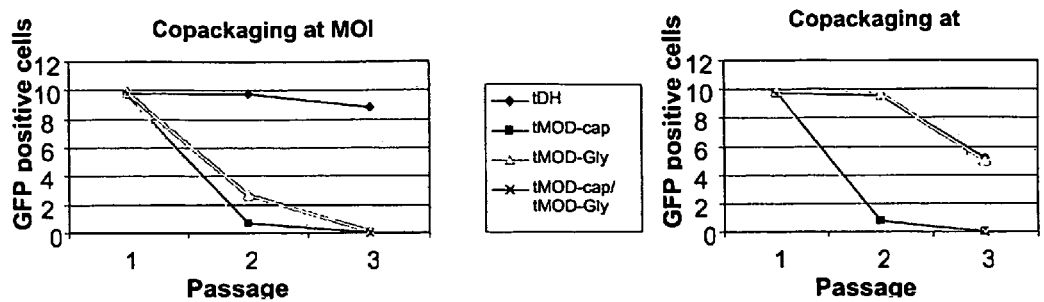
FIGS. 5A and 5B are graphs depicting co-packaging of helper constructs into particles and show that a modified 5' amplification sequence effectively reduces co-packaging of helper constructs comprising the modified sequence with minimal effects on particle yield.

Describe herein are compositions and methods for generating alphaviral particles (replicon particles). Specifically, modified 5' amplification sequences are described. The modified 5' amplification sequences find use in alphavirus structural protein constructs (e.g., helper constructs), packaging cell lines and the like.

The practice of the present invention will employ, unless otherwise indicated, conventional methods of chemistry, biochemistry, molecular biology, immunology and pharmacology, within the skill of the art. Such techniques are explained fully in the literature. See, e.g., *Remington's Pharmaceutical Sciences*, 18th Edition (Easton, Pa.: Mack Publishing Company, 1990); *Methods In Enzymology* (S. Colowick and N. Kaplan, eds., Academic Press, Inc.); and *Handbook of Experimental Immunology*, Vols. I-IV (D. M. Weir and C. C. Blackwell, eds., 1986, Blackwell Scientific Publications); Sambrook, et al., *Molecular Cloning: A Laboratory Manual* (2nd Edition, 1989); *Handbook of Surface and Colloidal Chemistry* (Birdi, K. S. ed., CRC Press, 1997); *Short Protocols in Molecular Biology*, 4th ed. (Ausubel et al. eds., 1999, John Wiley & Sons); *Molecular Biology Techniques: An Intensive Laboratory Course*, (Ream et al., eds., 1998, Academic Press); *PCR* (*Introduction to Biotechniques Series*), 2nd ed. (Newton & Graham eds., 1997, Springer Verlag); Peters and Dalrymple, *Fields Virology* (2d ed), Fields et al. (eds.), B. N. Raven Press, New York, N.Y.

All publications, patents and patent applications cited herein are hereby incorporated by reference in their entirety for all purposes.

As used in this specification and the appended claims, the singular forms "a," "an" and "the" include plural references unless the content clearly dictates otherwise. Thus, for example, reference to "a sequences" includes two or more such sequences.

Definitions

Prior to setting forth the invention definitions of certain terms that will be used hereinafter are set forth.

A "nucleic acid" or "polynucleotide" molecule can include, but is not limited to, prokaryotic RNA or DNA sequences, eukaryotic mRNA or other RNA, cDNA from eukaryotic mRNA or other RNA, genomic DNA sequences from eukaryotic (e.g., mammalian) DNA, synthetic DNA or RNA sequences, RNA transcribed from any of the foregoing DNAs and combinations of the foregoing. The term also captures sequences that include any of the known base analogs of DNA and RNA and includes modifications such as deletions, additions and substitutions (generally conservative in nature), to the native sequence. These modifications may be deliberate, as through site-directed mutagenesis, or may be accidental. Modifications of polynucleotides may have any number of effects including, for example, facilitating expression of the polypeptide product in a host cell. A polynucleotide can include both double- and single-stranded sequences and refers to, but is not limited to, cDNA from viral, prokaryotic or eukaryotic mRNA, genomic RNA and DNA sequences from viral (e.g. RNA and DNA viruses and retroviruses) or prokaryotic DNA, and synthetic DNA or RNA sequences. The term also captures sequences that include any of the known base analogs of DNA and RNA.

An "isolated nucleic acid molecule" or "isolated polynucleotide" refers to any polynucleotide that is separate and discrete from a whole organism with which it is normally associated and/or has been removed from its original environment (e.g., the natural environment if it is naturally occurring). For example, a naturally occurring polynucleotide is not isolated, but the same polynucleotide separated from some or all of the coexisting materials in the natural system is isolated. Such polynucleotide could be part of a vector and/or such polynucleotide could be part of a composition, and still be isolated in that the vector or composition is not part of its natural environment. Examples of isolated nucleic acid molecules are those that are not integrated into the genomic DNA of an organism, or, in the case of a virus, are separated from the complete virus genome as well as a chemically-synthesized nucleic acid molecule, or, a nucleic acid molecule that is produced by recombinant (e.g., PCR) techniques.

"Subgenomic RNA" refers to an RNA molecule of a length or size that is smaller than the genomic RNA from which it was derived. Subgenomic RNA is transcribed from an internal promoter whose sequences reside within the genomic RNA or its complement. In preferred embodiments, the subgenomic RNA is produced from an alphavirus vector construct, RNA vector replicon, or defective helper construct and encodes one or more alphavirus structural proteins or other heterologous sequences of interest. Generally, the subgenomic RNA resembles a typical mRNA with 5' and 3' end non-translated regions and a protein encoding open reading frame.

As used herein, the phrase "vector construct" generally refers to any assembly that is capable of directing the expression of a nucleic acid sequence(s) or gene(s) of interest. The vector construct typically includes a transcriptional promoter/enhancer or locus defining element(s), or other elements which control gene expression by other means such as alternate splicing, nuclear RNA export, post-translational modification of messenger, or post-transcriptional modification of protein. In addition, the vector construct typically includes a sequence which, when transcribed, is operably linked to the sequence(s) or gene(s) of interest and acts as a translation initiation sequence. For example, the vector may contain one or more 5' promoter sequences (e.g., DNA dependent RNA polymerase promoters) that initiate synthesis, including promoters derived from both prokaryotic and eukaryotic organisms, for example, the bacterial β-galactosidase and trpE promoters, and the eukaryotic viral simian virus 40 (SV40) (e.g., early or late), cytomegalovirus (CMV) (e.g., immediate early), Moloney murine leukemia virus (MoMLV) or Rous sarcoma virus (RSV) LTR, and herpes simplex virus (HSV) (thymidine kinase) promoters. The vector construct may also optionally include a signal that directs polyadenylation, a selectable marker, as well as one or more restriction sites and a translation termination sequence. Examples of vector constructs include ELVIS vectors, which comprise the cDNA complement of RNA vector constructs, RNA vector constructs themselves, alphavirus vector constructs, CMV vector constructs and the like.

"Alphavirus vector construct" refers to an assembly that is capable of directing the expression of a sequence or gene of interest. Such vector constructs are comprised of a 5' sequence that is capable of initiating transcription of an alphavirus RNA (also referred to as 5' conserved nucleotide sequence elements (CSE), or, 5' cis replication sequence which is capable of initiating transcription of an alphavirus RNA), as well as sequences which, when expressed, code for biologically active alphavirus nonstructural proteins (e.g., nsP1, nsP2, nsP3, nsP4), an alphavirus RNA polymerase recognition sequence (also referred to as 3'CSE, or, 3' cis replication sequence), and, optionally a polyadenylate tract. In addition, the vector construct may include a viral subgenomic "junction region" promoter, sequences from one or more structural protein genes or portions thereof, extraneous nucleic acid molecule(s) which are of a size sufficient to allow production of virus-like particles (e.g., replicon particles), a 5' promoter which is capable of initiating the synthesis of viral RNA from cDNA in vitro or in vivo (e.g., within a eukaryotic cell), a heterologous sequence to be expressed, and one or more restriction sites for insertion of heterologous sequences.

"Alphavirus RNA replicon vector," "RNA replicon vector," "replicon vector" or "replicon" refers to an RNA molecule that is capable of directing its own amplification or self-replication in vivo, within a target cell. To direct its own amplification, the RNA molecule should encode the enzyme(s) necessary to catalyze RNA amplification (e.g., alphavirus nonstructural proteins nsP1, nsP2, nsP3, nsP4) and also contain cis RNA sequences required for replication which are recognized and utilized by the encoded enzymes(s). An alphavirus RNA vector replicon should contain the following ordered elements: 5' viral or cellular sequences required for nonstructural protein-mediated amplification (may also be referred to as 5'CSE, or 5' cis replication sequence, or 5' viral sequences required in cis for replication, or 5' sequence which is capable of initiating transcription of an alphavirus), sequences which, when expressed, code for biologically active alphavirus nonstructural proteins (e.g., nsP1, nsP2, nsP3, nsP4), and 3' viral or cellular sequences required for nonstructural protein-mediated amplification (may also be referred as 3'CSE, or 3' viral sequences required in cis for replication, or an alphavirus RNA polymerase recognition sequence). The alphavirus RNA vector replicon may contain a means to express one or more heterologous sequence(s), such as for example, an IRES or a viral (e.g., alphaviral) subgenomic promoter (e.g., junction region promoter) which may, in certain embodiments, be modified in order to increase or reduce viral transcription of the subgenomic fragment, or to decrease homology with defective helper or structural protein expression cassettes, and one or more heterologous sequence(s) to be expressed. A replicon can also contain additional sequences, for example, one or more heterologous sequence(s) encoding one or more polypeptides (e.g., a protein-encoding gene or a 3' proximal gene) and/or a polyadenylate tract. The replicon should not contain sequences encoding all of the alphavirus structural proteins (capsid, E1, E2). Non-limiting examples of heterologous sequences that can be expressed by replicon vectors are described, for example in U.S. Pat. No. 6,015,686, incorporated by reference in its entirety herein, and include, for example, antigens, lymphokines, cytokines, etc.

A "packaging signal" or "packaging sequence" refers to a cis-acting sequence that is involved in incorporating nucleotides (e.g., genomic DNA or RNA) into viral particles (virions). Packaging signals from many viruses have been described. See, e.g., Youil R. et al. (2003) Human gene therapy 14(10):1017-1034; Beasley B E et al (2002) J. of Virology 76(10):4950-4960; Watanabe T et al. (2003) J. of Virology 77(19):10575-10583.

"Recombinant Alphavirus Particle" or "replicon particle" refers to a virion-like structural unit containing an alphavirus RNA vector replicon. Generally, a recombinant alphavirus particle comprises one or more alphavirus structural proteins, a lipid envelope and an RNA vector replicon. Preferably, the recombinant alphavirus particle contains a nucleocapsid structure that is contained within a host cell-derived lipid bilayer, such as a plasma membrane, in which alphaviral-encoded envelope glycoproteins are embedded. The particle may also contain other components (e.g., targeting elements, other viral structural proteins, or other receptor binding ligands) that direct the tropism of the particle from which the alphavirus was derived.

"Alphavirus structural protein expression cassette" refers to a vector construct that is capable expressing one or more alphavirus structural proteins. The alphavirus structural protein expression cassette may be a "defective helper construct" that is capable of RNA amplification or replication, and may express one or more alphavirus structural proteins in response to biologically active alphavirus nonstructural proteins supplied in trans. The defective helper construct typically contains the following ordered elements: a 5' amplification or cis replication sequence, a viral subgenomic junction region promoter, sequences which, when expressed, code for one or more biologically active alphavirus structural proteins (e.g., C, E3, E2, 6K, E1), 3' amplification or cis replication sequences, and a polyadenylate tract. The defective helper construct may also contain a 5' promoter which is capable of initiating the synthesis of viral RNA from cDNA in vitro or in vivo (e.g., in a eukaryotic cell), a 3' sequence which controls transcription termination, splice recognition sequences, a catalytic ribozyme processing sequence, a sequence encoding a selectable marker, and/or a nuclear export signal. A defective helper construct should not encode all four functional alphavirus nonstructural proteins.

The terms "5' viral or cellular sequences required for non-structural protein-mediated amplification" and "5' sequences required for nonstructural protein-mediated amplification" and "amplification sequences" and "5' amplification sequences" and "5' CSE" and "5' viral sequences required in cis for replication" and "5' sequence that is capable of initiating transcription of an alphavirus" are used interchangeably to refer to a functional element that provides a recognition site at which the virus or virus-derived vector synthesizes positive strand RNA. Thus, it may be a complement of the actual sequence contained within the virus or vector, which corresponds to the 3' end of the minus-strand RNA copy, which is bound by the nonstructural protein replicase complex, and possibly additional host cell factors, from which transcription of the positive-strand RNA is initiated. A wide variety of sequences have been utilized as amplification sequences including, for example, alphavirus 5'-end nontranslated regions (NTR) and other adjacent sequences, such as for example sequences through nucleotides 210, 250, 300, 350, 400, or 450 of an alphavirus genome. Alternatively, for example in the case of Sindbis (SIN) vectors, non-alphavirus nucleotides 10-75 for tRNA Asparagine (tRNAasp) (Schlesinger et al., U.S. Pat. No. 5,091,309) have been used.

As used herein, the term "5' modified amplification sequence" refers to a nucleotide (RNA or DNA) molecule comprising an amplification sequence as defined above, whose primary structure (sequence) has been modified (e.g., substitutions, additions, deletions) as compared to known amplification signals, such that the modified sequences are defective as a packaging signal but retain their amplification (replication) functionality. For example, modified amplification sequences may include reduced homology to packaging signals at the primary sequence level, while the secondary structure remains that of the original amplification sequence. Modified amplification sequences can further include additional sequences, so long as secondary structure and/or cis-acting amplification capability is maintained.

The term "3' Proximal Gene" refers to a nucleotide sequence encoding a protein, which is contained within a replicon vector, Eukaryotic Layered Vector Initiation System, defective helper RNA or structural protein expression cassette, and located within a specific position relative to another element. The position of this 3' proximal gene should be determined with respect to the 3' sequence required for nonstructural protein-mediated amplification (defined above), wherein the 3' proximal gene is the protein-encoding sequence 5' (upstream) of, and immediately preceding this element.

The term "viral subgenomic promoter" refers to a sequence of virus origin that, together with required viral and cellular polymerase(s) and other factors, permits transcription of an RNA molecule of less than genome length. For an alphavirus (alphaviral) subgenomic promoter or alphavirus (alphaviral) subgenomic junction region promoter, this sequence is derived generally from the region between the nonstructural and structural protein open reading frames (ORFs) and normally controls transcription of the subgenomic mRNA. Typically, the alphavirus subgenomic promoter consists of a core sequence that provides most promoter-associated activity, as well as flanking regions (e.g., extended or native promoter) that further enhance the promoter-associated activity. The subgenomic promoter may be a complement of the actual sequence contained within the virus or vector, which corresponds to the region in a minus-strand RNA copy and which promotes transcription initiation of the positive-strand subgenomic mRNA. For example, in the case of the alphavirus prototype, Sindbis virus, the normal subgenomic junction region promoter typically begins at approximately nucleotide number 7579 and continues through at least nucleotide number 7612 (and possibly beyond). At a minimum, nucleotides 7579 to 7602 are believed to serve as the core sequence necessary for transcription of the subgenomic fragment.

The terms "3' viral or cellular sequences required for non-structural protein-mediated amplification" or "3' sequences required for nonstructural protein-mediated amplification" are used interchangeably with the terms 3'CSE, or 3' cis replication sequences, or 3' viral sequences required in cis for replication, or an alphavirus RNA polymerase recognition sequence. This sequence is a functional element that provides a recognition site at which the virus or virus-derived vector begins replication (amplification) by synthesis of the negative RNA strand. A wide variety of sequences may be utilized for this function. For example, the sequence may include a complete alphavirus 3'-end non-translated region (NTR), such as for example, with SIN, which would include nucleotides 11,647 to 11,703, or a truncated region of the 3' NTR, which still maintains function as a recognition sequence (e.g., nucleotides 11,684 to 11,703). See, e.g., U.S. Pat. No. 6,329,210. Other examples of sequences that may be utilized in this context include, but are not limited to, non-alphavirus or other sequences that maintain a similar functional capacity to permit initiation of negative strand RNA synthesis (e.g., sequences described in George et al., (2000) J. Virol. 74:9776-9785).

"Stable transformation" refers to the introduction of a nucleic acid molecule into a living cell, and long-term or permanent maintenance of that nucleic acid molecule in progeny cells through successive cycles of cell division. The nucleic acid molecule may be maintained in any cellular compartment, including, but not limited to, the nucleus, mitochondria, or cytoplasm. In preferred embodiments, the nucleic acid molecule is maintained in the nucleus. Maintenance may be intrachromosomal (integrated) or extrachromosomal, as an episomal event.

"Alphavirus packaging cell line" refers to a cell which contains an alphavirus structural protein expression cassette and which produces recombinant alphavirus particles after introduction of an alphavirus vector construct, RNA vector replicon, eukaryotic layered vector initiation system (e.g., U.S. Pat. No. 5,814,482), or recombinant alphavirus particle. The parental cell may be of mammalian or non-mammalian origin. Within preferred embodiments, the packaging cell line is stably transformed with the structural protein expression cassette.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

Two or more polynucleotide sequences can be compared by determining their "percent identity." Two or more amino acid sequences likewise can be compared by determining their "percent identity." The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be extended to use with peptide sequences using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An implementation of this algorithm for nucleic acid and peptide sequences is provided by the Genetics Computer Group (Madison, Wis.) in their BestFit utility application. The default parameters for this method are described in the Wisconsin Sequence Analysis Package Program Manual, Version 8 (1995) (available from Genetics Computer Group, Madison, Wis.). Other equally suitable programs for calculating the percent identity or similarity between sequences are generally known in the art.

For example, percent identity of a particular nucleotide sequence to a reference sequence can be determined using the homology algorithm of Smith and Waterman with a default scoring table and a gap penalty of six nucleotide positions. Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated, the "Match" value reflects "sequence identity." Other suitable programs for calculating the percent identity or similarity between sequences are generally known in the art, such as the alignment program BLAST, which can also be used with default parameters. For example, BLASTN and BLASTP can be used with the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: www.ncbi.nlm.gov under the directory cgi-bin/BLAST.

One of skill in the art can readily determine the proper search parameters to use for a given sequence in the above programs. For example, the search parameters may vary based on the size of the sequence in question. Thus, for example, a representative embodiment of the present invention would include an isolated polynucleotide having X contiguous nucleotides, wherein (i) the X contiguous nucleotides have at least about 50% identity to Y contiguous nucleotides derived from any of the sequences described herein, (ii) X equals Y, and (iii) X is greater than or equal to 6 nucleotides and up to 5000 nucleotides, preferably greater than or equal to 8 nucleotides and up to 5000 nucleotides, more preferably 10-12 nucleotides and up to 5000 nucleotides, and even more preferably 15-20 nucleotides, up to the number of nucleotides present in the full-length sequences described herein (e.g., see the Sequence Listing and claims), including all integer values falling within the above-described ranges.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

The term "secondary structure" refers to the conformation (secondary or tertiary structure) of a polynucleotide. For example, single stranded RNA molecules commonly adopt secondary structure such as hairpins, stem-and-loop structure and the like. The secondary structure of any given polynucleotide can be predicted from the primary sequence using a number of algorithms, for example the mfold package for RNA and DNA secondary structure prediction as described in Zucker et al. "Algorithms and thermodynamics for RNA secondary structure prediction: a practical guide," available on the internet.

The term "derived from" is used to identify the alphaviral source of molecule (e.g., polynucleotide, polypeptide). A first polynucleotide is "derived from" second polynucleotide if it has the same or substantially the same basepair sequence as a region of the second polynucleotide, its cDNA, complements thereof, or if it displays sequence identity as described above or if it encodes a polypeptide that is the same or substantially the same as a polypeptide encoded by the second polynucleotide. Thus, a polynucleotide is "derived from" a particular alphavirus (e.g., species) if it has (i) the same or substantially the same sequence as at least a portion of the particular alphavirus sequence or (ii) encodes a polypeptide exhibiting sequence identity (e.g., greater than 50% percent identity as described above) to of any to polypeptides of that alphavirus as described above. Thus, sequences described herein may be derived from one or more alphaviruses (SIN, VEE, SFV, etc.), which can be readily obtained given the disclosure provided herein from naturally occurring sources, or from depositories (e.g., the American Type Culture Collection, Rockville, Md.). Representative examples of suitable alphaviruses are described in more detail in U.S. Pat. No. 5,843,723 and PCT Publication No. WO 97/38087.

Typical "control elements", include, but are not limited to, transcription promoters, transcription enhancer elements, transcription termination signals, polyadenylation sequences (located 3' to the translation stop codon), sequences for optimization of initiation of translation (located 5' to the coding sequence), translation termination sequences, 5' sequence required for nonstructural protein-mediated amplification, 3' sequence required for nonstructural protein-mediated amplification, and means to express one or more heterologous sequences (e.g., subgenomic junction region promoter), see e.g., McCaughan et al. (1995) *PNAS USA* 92:5431-5435; Kochetov et al (1998) *FEBS Letts.* 440:351-355.

"Eukaryotic Layered Vector Initiation System" refers to a polynucleotide that comprises an assembly that is capable of directing the expression of a sequence or gene of interest. The eukaryotic layered vector initiation system should contain a 5' promoter that is capable of initiating in vivo (i.e. within a eukaryotic cell) the synthesis of RNA from cDNA, and a nucleic acid vector sequence (e.g., viral vector) that is capable of directing its own replication in a eukaryotic cell and also expressing a heterologous sequence. Preferably, the nucleic acid vector sequence is an alphavirus-derived sequence and is comprised of 5' viral or cellular sequences required for non-structural protein-mediated amplification (also referred to as 5'CSE, or 5' cis replication sequence, or 5' viral sequences required in cis for replication, or 5' sequence which is capable of initiating transcription of an alphavirus), as well as sequences which, when expressed, code for biologically active alphavirus nonstructural proteins (e.g., nsP1, nsP2, nsP3, nsP4), and 3' viral or cellular sequences required for nonstructural protein-mediated amplification (also referred to as 3'CSE, or 3' viral sequences required in cis for replication, or an alphavirus RNA polymerase recognition sequence). In addition, the vector sequence may include a means to express heterologous sequence(s), such as for example, a viral (e.g., alphaviral) subgenomic promoter (e.g., junction region promoter) which may, in certain embodiments, be modified in order to prevent, increase, or reduce viral transcription of the subgenomic fragment, or to decrease homology with defective helper or structural protein expression cassettes, and one or more heterologous sequence(s) to be expressed. Preferably the heterologous sequence(s) comprises a protein-encoding gene and said gene is the 3' proximal gene within the vector sequence. The eukaryotic-layered vector initiation system may also contain a polyadenylation sequence, splice recognition sequences, a catalytic ribozyme processing sequence, a nuclear export signal, and a transcription termination sequence. Preferably, the eukaryotic layered vector initiation system contains sequences encoding all alphavirus structural proteins (capsid, E2 and E1). A "hybrid" ELVIS refers to an assembly that includes polynucleotide sequences derived from two or more alphaviruses.

As discussed in more detail below, the present invention includes, but is not limited to, sequences suitable for use in the alphavirus constructs; construct comprising these sequences; packaging cell lines; methods of packaging recombinant alphavirus particles; methods of suppressing co-packaging during vector packaging.

General Overview

The present invention relates to modified 5' amplification sequences for use in the generation of alphavirus-based particles, particular sequences that have been engineered for use in structural protein expression cassettes. The modified 5' amplification sequences described herein reduce co-packaging events during the generation of alphavirus replicon particles and, therefore, find use in packaging cell lines, and methods of generating alphavirus replicon particles.

Currently, alphavirus replicon particles are typically generated using a multi-construct system that separates the various elements required for particle formation. Separation of these elements into different constructs reduces the risk of generating wild type, infectious virus. The systems typically include a replicon vector, which contains elements necessary for its own intracellular replication (e.g., nonstructural protein coding sequences) but lacks elements needed for production of progeny particles (e.g., structural protein coding sequences), and one or more structural protein expression cassettes (e.g., defective helper construct(s)) that encode the structural proteins (e.g., capsid, glycoproteins) required for packaging. The replicon constructs and the defective helper constructs may be DNA- and/or RNA-based. See, e.g., Polo et al. (1999) *Proc. Nat'l Acad. Sci USA* 96:4598-4603; U.S. Pat. Nos. 6,465,634; 6,426,196; 6,376,236; 6,342,372; 6,015,686; and 5,843,723.

As depicted in FIG. 1, two defective helper constructs may be used to provide the structural genes for packaging of the replicon RNA. The use of two separate defective helpers may be preferable, as the risk of generating replication-competent virus (RCV) is reduced. See, e.g., U.S. Pat. No. 6,426,196. The helper constructs contain cis elements necessary for their own amplification by the nonstructural produced in trans and for expression of the structural protein genes, but lack alphavirus nonstructural protein genes. To reduce co-packaging of helpers into the replicon particles, the cis-acting alphavirus packaging signal is(are) also typically deleted from the helper construct(s). Co-packaging refers both to the generation of particles containing one or more helper RNAs but no replicon RNA constructs (also referred to as "abortive" particles) as well as to the generation of particles that contain one or more helper sequences in addition the replicon sequences. Both forms of co-packaging are undesirable. In particular, the presence of abortive particles can interfere with the infectivity of the replicon particles, effectively reducing the efficiency of particle infection. Similarly, co-packaging of replicon and helper sequences may result in the production of new particles upon infection of naïve cells and these particles may behave more like replication-competent virus (RCV), including undesirable effects of virus.

Various cis-elements involved in replication (i.e., 5' amplification sequences) may be incorporated into defective helper constructs, including, for example, native (wild-type) alphavirus 5' sequences from homologous virus, native alphavirus 5' sequences from heterologous virus, non-native defective interfering (DI) alphavirus 5' sequences from homologous virus, non-native DI alphavirus 5' sequences from heterologous virus, non-alphavirus derived viral sequence (e.g., togavirus, plant virus), and cellular RNA derived sequences (e.g., tRNA element) (e.g., Monroe et al., *PNAS* 80:3279-3283, 1983; Niesters et al., *J. Virol.* 64:4162-4168, 1990; Niesters et al., *J. Virol.* 64:1639-1647, 1990; Tsiang et al. (1988) *J. Virol.* 62(1):47-53).

Although these 5' amplification sequences may serve to mediate replication, each of the 5' amplification sequences, including non-alphavirus derived sequences such as tRNAasp sequences, may also exhibit undesirable co-packaging effects. See, e.g., Bredenbeek et al. (1993) *J. Virol.* 67:6439-6446; Tsaing et al. (1985) *J. Virol.* 54:38-44.

Figure 6:
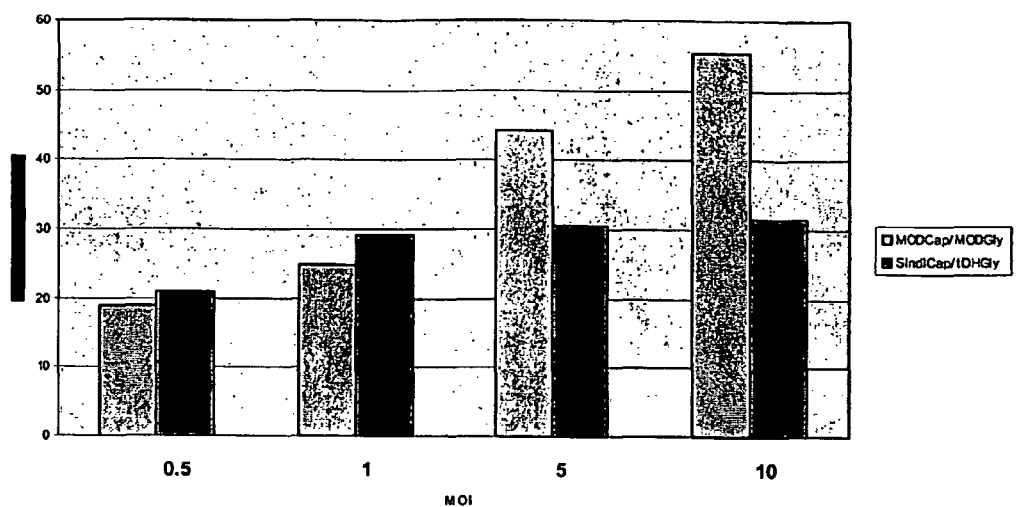
FIG. 6 is a graph depicting infectivity of particles made with using structural cassettes containing either modified (light gray) amplification sequences or unmodified tRNA sequences (dark gray). MOI is shown along the horizontal axis.

Described herein are compositions and methods that reduce or eliminate packaging of unwanted sequences into alphavirus replicon particles, while, at the same time, allowing for efficient replication of the alphavirus vectors. In this regard, the present inventors have discovered that the sequences typically used as replication signals for the alphavirus structural protein cassettes that are used in packaging alphavirus replicon particles often contain sequences that can undesirably serve as packaging signals. Specifically, it appears that the primary structure (sequence) of the 5' amplification sequence plays a role in unwanted co-packaging but not in the desirable replication (amplification) functions that are mostly dependent on the secondary structure of the same region. (FIGS. 4A and 4B). By designing a molecule that maintains a secondary structure that is characteristic of functional amplification sequences, but eliminates primary sequence homology to known packaging signals, the present invention allows for novel compositions and methods that effectively and efficiently accomplish replication of the structural proteins helper constructs needed for alphavirus packaging and reduce or eliminate co-packaging of the helper constructs. In addition, helper constructs comprising the modified 5' amplification sequences described herein produce replicon particles with greater infectivity than those produced with helper constructs including tRNA-containing sequences. (FIG. 6).

Modified 5' Amplification Sequences

The modified 5' amplification sequences described herein are sequences that are functional amplification sequences but essentially unable to serve as packaging signals. Thus, the particular sequence of the modified 5' amplification sequences described herein can vary greatly, so long as they are essentially unable to serve as packaging signals and functional as amplification (replication) signals.

The modified 5' amplification sequences described herein are typically between 10 and 150 nucleotides in length (or any length therebetween), more preferably between about 30 and 100 nucleotides in length (or any length therebetween), and even more preferably between about 40 and 80 nucleotides in length (or any length therebetween).

In general, production of modified 5' sequences involves both sequence and structural analysis of a polynucleotide. Typically, the process begins by comparing the primary sequence of a known 5' amplification sequence (e.g., tRNAasp) to known packaging signals. The cis-acting 5' amplification sequences described herein can be derived from any number of sources, for example, from native alphavirus 5' sequences from any virus, native alphavirus 5'-end from heterologous virus, non-native DI alphavirus 5'-end from homologous virus, non-native DI alphavirus 5'-end from heterologous virus, non-alphavirus derived viral sequence (e.g., togavirus, plant virus), and cellular RNA derived sequence (e.g., tRNA element) (e.g., Monroe et al., *PNAS* 80:3279-3283, 1983; Niesters et al., *J. Virol.* 64:4162-4168, 1990; Niesters et al., *J. Virol.* 64:1639-1647, 1990). The sequences of these and other functional 5' amplification sequences and packaging signals are known publicly available in any number of databases.

Thus, the process of obtaining a modified 5' amplification sequence with a predetermined secondary structure can begin by analysis of known 5' amplification sequences. Sequences within 5' amplification sequences that function as packaging signals can be identified by any suitable means, for example, by alignment with known packaging signals to determine regions of high homology. For instance, as shown in FIG. 2, nucleotides 37 to 58 of the known tRNA-asp sequence (Monroe et al. (1983) *Proc. Nat'l Acad. Sci USA* 80:3279-3282) exhibits significant homology (>80%) to nucleotides 1029-1050 of Sindbis (SIN) (GenBank Accession No. NC 001547, Strauss et al. (1984) *Virol* 133:92-110), which nucleotides are known to be involved in packaging. It is to be understood that wild-type SIN is used solely for purposes of exemplifying aspects of the invention and that any packaging signal sequence can be chosen for comparison.

Once identified, the packaging signals may be made defective by any suitable means, for example by altering the primary sequence of the 5' amplification signal so as to decrease homology to known packaging signals. (Example 1). Sequences can be altered by mutagenesis, substitution, insertion and/or deletion of one or more nucleotides so that the primary sequence does not function as a packaging signals.

The degree of homology at the primary sequence levels as between unmodified and modified sequences can vary greatly, so long as the packaging signal is defective. For example, in the regions identified as putative packaging signals, homology, at the primary sequence level, as between modified and unmodified sequences may be as much as 99%, although it is preferably between about 90% and 99% or between about 90% and 95%, more preferably less than about 90%, more preferably less than 80% and even more preferably less than 70% homology to regions of the same length of a known packaging signal. For instance, as shown in FIG. 3, exemplary modified 5' amplification sequences (SEQ ID NOs:4-16) were generated by modifying the region of tRNA-asp that exhibited homology to the wild-type SIN packaging signal, such that the homology in this region is greatly reduced (e.g., from greater than 80% to less than 70% all cases and less than 40% in some cases (e.g., SEQ ID NOs:4, 11, 14 and 15)). While the sequences in FIG. 3 are shown as DNA sequences, it will be apparent that for use in RNA-based vectors the sequences are replaced by the corresponding RNA residues, i.e., T is replaced by U.

The modification(s) to the primary sequence are preferably made such that the secondary structure of the polynucleotide remains substantially similar to the unmodified 5' amplification sequence. As noted above, single stranded nucleic acid molecules (e.g., RNA) commonly adopt secondary structure such as hairpins, stem-and-loop structure and the like. Techniques for predicting secondary structure of any given nucleic acid sequence are readily available and described, for example in Zucker et al. "Algorithms and Thermodynamics for RNA secondary structure prediction: a practical guide" and Macke et al. (2001) *Nucleic Acids Res* 29(22):4724-4735.

Thus, mutations are introduced into putative packaging signal sequences to generate sequences having a different primary sequence but having a secondary structure of known 5' amplification sequences (e.g., secondary structure of tRNAasp as shown in FIG. 4A).

Alternatively, the modified 5' amplification sequences described herein can be synthetic sequences generated to have a secondary structure similar to known amplification sequences.

Therefore, although the modified 5' amplification sequences disclosed herein form secondary structures characteristic of cis-acting 5' amplification sequences, they are defective as packaging signals, presumably due to the decreased homology to known packaging signals at the primary structure level.

In certain embodiments, modified 5' amplification sequences, as disclosed herein, contain additional modifications in regions outside of the packaging signal. The modified 5' amplification sequences described herein can be used in the production of defective helper constructs, packaging cell lines and the like.

Additional Components of Structural Protein Cassettes (e.g., Helper Constructs)

In certain aspects, the modified 5' amplification sequences described herein form part of a structural protein cassette or defective helper construct. Thus, in addition to the modified 5' amplifications sequences, the helper constructs described herein will typically include a variety of nucleic acid sequences, both coding and non-coding sequences. It will be apparent that the compositions described herein generally comprise less than a complete alphavirus genome (e.g., contain less than all of the coding and/or non-coding sequences contained in a genome of an alphavirus) in a single polynucleotide.

The helper constructs comprising a modified 5' amplification sequence as described herein typically also include one or more sequences coding for various alphavirus polypeptides, for example one or more structural (e.g., caspid, envelope glycoprotein) alphavirus polypeptides. Structural proteins surrounding (and in some cases, interacting with) the alphavirus replicon or vector polynucleotide component(s) include both capsid and envelope glycoproteins. See, e.g., Strauss et al. (1994) *Microbiol. Rev.,* 58:491-562. In most instances, the polynucleotide component(s) are surrounded by the capsid protein(s), which form nucleocapsids. In turn, the nucleocapsid protein is surrounded by a lipid envelope containing the envelope protein(s). The capsid protein is the N-terminal protein of the alphavirus structural polyprotein, and following processing from the polyprotein, interacts with alphavirus RNA containing the packaging signal and other capsid protein monomers to form nucleocapsid structures. Alphavirus envelope glycoproteins (e.g., E2, E1) protrude from the enveloped particle as surface "spikes", which are functionally involved in receptor binding and entry into the target cell.

The additional sequences may be coding or non-coding. Non-limiting examples of non-coding sequences include a means for expressing a 3' proximal gene (control elements such as promoters and the like, for example, a native alphavirus subgenomic promoter from homologous virus, a native alphavirus subgenomic promoter from heterologous virus, a core alphavirus subgenomic promoter (homologous or heterologous), minimal sequences upstream or downstream from core subgenomic promoter, mutations/deletions/additions of core or native subgenomic promoter, a non-alphavirus derived compatible subgenomic promoter (e.g. plant virus), an internal ribosome entry site (IRES), and/or a ribosomal readthrough element (e.g., BiP); subgenomic mRNA 5'-end nontranslated region (subgenomic 5' NTR), one or more additional 5' or 3' sequences required for nonstructural protein-mediated amplification (U.S. Pat. Nos. 5,843,723; 6,015,694; 5,814,482; PCT publications WO 97/38087; WO 00/61772), a 3' proximal gene (e.g., a heterologous sequence, polypeptide encoding sequence). See, also, Kuhn et al. (1990) J. Virol. 64:1465-1476); and/or a polyadenylation sequence (e.g., within 3' sequences, see, e.g., George et al. (2000) J. Virol. 74:9776-9785).

The coding and non-coding sequences used in the helper constructs described herein may include sequences derived from one or more alphaviruses and/or non-alphaviral sources (e.g., alphavirus, togavirus, plant virus). Generally, while nucleotide and amino acid numbering is somewhat different between alphaviruses, primarily due to slight differences in polyprotein lengths, alignments amongst or between sequences from different alphaviruses provides a means to identify similar regions in other alphaviruses (see representative alignment in Kinney et al. (1989) Virology 170:19-30 and Strauss et al. (1984) *Virol* 133:92-110 for an exemplary wild-type SIN genome of 11,703 nucleotides in length, to which any other alphavirus genome can be aligned). In certain embodiments, the helper constructs include sequences derived from two or members of the alphavirus genus. Certain of the alphavirus sequences described herein are described in further detail in co-owned International Publication WO 02/099035, the disclosure of which is hereby incorporated by reference herein in its entirety.

Further, one or more of the helper construct sequences may include one or more modifications as compared to wild type. Modifications to alphavirus coding sequences may include, but are not limited to nucleotide mutations, deletions, additions, or sequence substitutions, in whole or in part, such as for example, hybrid nonstructural protein comprising sequences from one or more alphavirus and/or another virus (e.g., alphavirus, other togavirus, plant virus).

Alphavirus Packaging Cell Lines

Within further embodiments of the invention, alphavirus packaging cell lines are provided. In particular, within one aspect of the present invention, alphavirus packaging cell lines are provided wherein the alphaviral structural proteins, supplied in trans from one or more expression vectors carrying one or more modified 5' amplification sequences as described herein that are preferably stably integrated, are able to encapsidate transfected, transduced, or intracellularly produced vector RNA transcripts in the cytoplasm and release infectious packaged replicon vector particles through the cell membrane, thus creating an alphavirus vector producing (packaging) cell line (PCL).

For example, alphavirus packaging cell lines are provided wherein the viral structural proteins are supplied in trans from one or more stably transformed expression vectors (structural protein expression cassettes) as described herein (e.g., including a modified 5' amplification sequence), and are able to encapsidate transfected, transduced, or intracellularly produced vector RNA transcripts in the cytoplasm and release infectious packaged vector particles through the cell membrane. In certain embodiments, the structural proteins necessary for packaging are synthesized at high levels only after induction by the RNA vector replicon itself or some other provided stimulus, and the transcripts encoding these structural proteins are capable of cytoplasmic amplification in a manner that will allow expression levels sufficient to mimic that of a natural viral infection. Furthermore, in other embodiments, expression of a selectable marker is operably linked to the structural protein expression cassette. Such a linked selectable marker allows efficient generation of functional, stably transformed PCL.

For example, alphavirus RNA vector replicon molecules of the desired phenotype to be packaged, which are themselves capable of autocatalytic replication (e.g., the replicon contains all the elements (cis and trans) needed for replication in the permissive cells) in the cell cytoplasm, can be introduced into the packaging cells as in vitro transcribed RNA, recombinant alphavirus particles, or as alphavirus cDNA vector constructs. The RNA vector replicon molecules then replicate to high levels, stimulate amplification of the structural protein gene transcript(s) and subsequent structural protein expression, and are subsequently packaged by the viral structural proteins, yielding infectious vector particles. The intracellular expression of alphavirus proteins and/or vector RNA above certain levels may result in cytotoxic effects in packaging or producer cell lines. Therefore, within certain embodiments of the invention, it may be desirable for these elements to be derived from virus variants selected for reduced cytotoxicity of their expressed structural proteins, reduced inhibition of host macromolecular synthesis, and/or the ability to establish persistent infection.

To optimize vector packaging cell line performance and final vector titer, successive cycles of gene transfer and vector packaging may be performed, as described in detail in U.S. Pat. No. 6,391,632, incorporated by reference in its entirety herein. Similarly, PCLs can be produced using stably integrated or episomally maintained DNA expression vector, as described in detail in U.S. Pat. No. 6,391,632, incorporated by reference in its entirety herein.

Alphavirus RNA vector molecules, capable of replicating in the cytoplasm of the packaging cell, can be produced initially utilizing, for example, an SP6 RNA polymerase system to transcribe in vitro a cDNA vector clone encoding the gene of interest within an alphavirus replicon vector containing functional nonstructural proteins. Vector RNA transcripts are then transfected into the alphavirus packaging cell line, such that the vector RNA replicates to high levels, and is subsequently packaged by the viral structural proteins, yielding infectious replicon vector particles.

Within other embodiments, PCLs may be produced using pseudotyped alphavirus vector particles, as described in U.S. Pat. No. 5,789,245 incorporated by reference in its entirety herein. U.S. Pat. No. 5,789,245 also describes additional modifications that may be made to PCLS, for example modifications whereby the structural proteins necessary for packaging are synthesized only after induction by the RNA vector itself or some other stimulus.

A variety of different cells known in the art can be used in the practice of the present invention; for example, mammalian cells, avian cells, baculoviruses, bacteria, and yeast cells. Insect cell expression systems, such as baculovirus systems, are known to those of skill in the art and described in, e.g., Summers and Smith, *Texas Agricultural Experiment Station Bulletin* No. 1555 (1987). Materials and methods for baculovirus/insert cell expression systems are commercially available in kit form from, inter alia, Invitrogen, San Diego Calif. Avian cell expression systems are also known to those of skill in the art and described in, e.g., U.S. Pat. Nos. 5,340,740; 5,656,479; 5,830,510; 6,114,168; and 6,500,668; European Patent No. EP 0787180B; European Patent Application No. EP03291813.8; WO 03/043415; and WO 03/076601. Similarly, bacterial and mammalian cell expression systems are also known in the art and described in, e.g., *Yeast Genetic Engineering* (Barr et al., eds., 1989) Butterworths, London.

A number of appropriate host cells for use with the above systems are also known. For example, mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (e.g., Hep G2), Madin-Darby bovine kidney ("MDBK") cells, as well as others. Mammalian sources of cells include, but are not limited to, human or non-human primate (e.g., PERC.6 cells which are described, for example, in WO 01/38362 and WO 02/40665, incorporated by reference herein in their entireties, as well as deposited under ECACC deposit number 96022940), MRC-5 (ATCC CCL-171), WI-38 (ATCC CCL-75), fetal rhesus lung cells (ATCC CL-160), human embryonic kidney cells (293 cells, typically transformed by sheared adenovirus type 5 DNA), VERO cells from monkey kidneys), horse, cow (e.g., MDBK cells), sheep, dog (e.g., MDCK cells from dog kidneys, ATCC CCL34 MDCK (NBL2) or MDCK 33016, deposit number DSM ACC 2219 as described in WO 97/37001), cat, and rodent (e.g., hamster cells such as BHK21-F, HKCC cells, or Chinese hamster ovary cells (CHO cells)), and may be obtained from a wide variety of developmental stages, including for example, adult, neonatal, fetal, and embryo.

Avian sources of cells include, but are not limited to, chicken cells (e.g., chicken embryonic stem cells (e.g., EBx® cells), chicken embryonic fibroblasts, chicken embryonic germ cells)). Similarly, bacterial hosts such as *E. coli*, *Bacillus subtilis*, and *Streptococcus* spp., will find use with the present expression constructs. Yeast hosts useful in the present invention include, inter alia, *Saccharomyces cerevisiae*, *Candida albicans*, *Candida maltosa*, *Hansenual polymorpha*, *Kluyveromyces fragilis*, *Kluyveromyces lactis*, *Pichia guillerimondii*, *Pichia pastoris*, *Schizosaccharomyces pombe* and *Yarrowia lipolytica*. Insect cells for use with baculovirus expression vectors include, inter alia, *Aedes aegypti*, *Autographa californica*, *Bombyx mori*, *Drosophila melanogaster*, *Spodoptera frugiperda*, and *Trichoplusia ni*.

Methods of Packaging Recombinant Alphavirus Particles

As provided by the invention, generation (packaging) of recombinant alphavirus vector particles (replicon particles) may be readily accomplished by, for example, co-transfection of replicon vectors with structural protein expressions cassettes, complementing vector and defective helper (DH) molecules derived from in vitro transcribed RNA, or plasmid DNA, or by co-infection with virus (see Bredenbeek et al., J. Virol. 67:6439-6446, 1993, Dubensky et al., J. Virol 70:508-519, 1996 and U.S. Pat. Nos. 5,814,482, 5,739,026, 5,766, 602, 5,789,245 and 5,792,462, incorporated by reference in their entireties herein. Compositions and methods for packaging of alphavirus vectors is also described in U.S. Pat. Nos. 6,329,201 and 6,242,259, incorporated by reference in their entireties herein.

Alternatively, vector particles may be generated by introduction of vector RNA into stable alphavirus packaging cell lines described above. Briefly, such PCL and their stably transformed structural protein expression cassettes can be derived using methods essentially as described within U.S. Pat. No. 5,789,245, particularly using constructs comprising modified 5' amplification sequences as described herein. For example, the production of recombinant alphavirus vector particles by PCL may be accomplished following introduction of alphavirus-based vector molecules into the PCL, the vectors being derived from in vitro transcribed RNA, plasmid DNA, or previously obtained recombinant alphavirus particles, incubating the PCL for a under conditions and for a time necessary for vector particle packaging, and harvesting of the packaged vector particles. As shown in the detailed examples provided herein, utilization of the novel 5' amplification sequences of the present invention for efficient vector packaging in such approaches is readily accomplished.

Co-packaging could be assayed by serial passage of replicon particles in naïve cultured cells (e.g., cells that are not packaging cells). The replicon particles without co-packaging will not produce new progeny replicon particles after infecting the naïve cells, while replicon particle with co-packaging will continuously produce new replicon particles. Also under the microscope, co-packaging containing replicon may produce focus-like patterns of ocytopathic effect (CPE), resulting from direct particle spreading from adjacent cells. Co-packaging also may be determined by infection of naïve cells with replicon particles and testing for expression of one or more alphavirus structural proteins in the infected cells (e.g., by western blot).

Heterologous Sequences

As noted above, the modified 5' amplification sequences (and constructs comprising these sequences) described herein can be used in a wide range of applications. For example, modified 5' amplification sequences can be used in helper constructs for producing alphavirus replicon particles. The replicon particles can include a wide variety of heterologous sequences, for example, sequences which encode palliatives such as lymphokines or cytokines, toxins, and prodrug converting enzyme, sequences which encode antigens that stimulate an immune response, ribozymes or antisense sequences, sequences which encode proteins for therapeutic application such as growth or regulatory factors, and sequences which encode proteins that assist or inhibit an immune response.

Preferably, the nucleotide sequences should be of a size sufficient to allow efficient production of viable vector particles. Within the context of the present invention, the production of any measurable titer of recombinant alphavirus particles, for example, by transfer of expression assay, titering cell line assay, reporter assay, or plaque assay on appropriate susceptible monolayers, is considered to be "production of viable vector particles". This may be, at a minimum, an alphavirus vector construct that does not contain any additional heterologous sequence. However, within other embodiments, the vector construct may contain additional heterologous or foreign sequences. Within preferred embodiments, the heterologous sequence can comprise a heterologous sequence of at least about 100 bases, 2 kb, 3.5 kb, 5 kb, 7 kb, or even a heterologous sequence of at least about 8 kb. The above-described heterologous sequences may be readily obtained from a variety of sources, including for example, depositories such as the American Type Culture Collection (ATCC, Rockville, Md.), or from commercial sources such as British Bio-Technology Limited (Cowley, Oxford, England). Alternatively, cDNA sequences which encode the above-described heterologous sequences may be obtained from cells which express or contain the sequences, utilizing standard procedures known in the art. In addition, heterologous sequences also may be synthesized, for example, on an Applied Biosystems, Inc. DNA synthesizer.

Representative examples of suitable heterologous sequences are discussed in more detail within U.S. Pat. No. 5,843,723.

Non-limiting examples of heterologous sequence encoding immunogenic proteins include proteins derived from one or more of the following set forth below:

Bacterial Antigens such as *N. meningitides*: a protein antigen from *N. meningitides* serogroup A, C, W135, Y, and/or B (1-7); an outer-membrane vesicle (OMV) preparation from *N. meningitides* serogroup B. (8, 9, 10, 11); a saccharide antigen, including LPS, from *N. meningitides* serogroup A, B, C W135 and/or Y, such as the oligosaccharide from serogroup C (see PCT/US99/09346; PCT IB98/01665; and PCT IB99/00103); *Streptococcus pneumoniae*: a saccharide or protein antigen, particularly a saccharide from *Streptooccus pneumoniae*; *Streptococcus agalactiae*: particularly, Group B *streptococcus* antigens; *Streptococcus pyogenes*: particularly, Group A *streptococcus* antigens; *Enterococcus faecalis* or *Enterococcus faecium* (particularly a trisaccharide repeat or other *Enterococcus* derived antigens provided in U.S. Pat. No. 6,756,361); *Helicobacter pylori*: including: Cag, Vac, Nap, HopX, HopY and/or urease antigen; *Bordetella pertussis*: such as petussis holotoxin (PT) and filamentous haemagglutinin (FHA) from *B. pertussis*, optionally also combination with pertactin and/or agglutinogens 2 and 3 antigen; *Staphylococcus aureus*: including *S. aureus* type 5 and 8 capsular polysaccharides optionally conjugated to nontoxic recombinant *Pseudomonas aeruginosa* exotoxin A, such as StaphVAX™, or antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and/or membrane-damaging toxins (optionally detoxified) that lyse eukaryotic cell membranes (hemolysins, leukotoxin, leukocidin); *Staphylococcus epidermis*: particularly, *S. epidermidis* slime-associated antigen (SAA); *Staphylococcus saprophyticus*: (causing urinary tract infections) particularly the 160 kDa hemagglutinin of *S. saprophyticus* antigen; *Pseudomonas aeruginosa*: particularly, endotoxin A, Wzz protein, *P. aeruginosa* LPS, more particularly LPS isolated from PAO1 (O5 serotype), and/or Outer Membrane Proteins, including Outer Membrane Proteins F (OprF) (Price et al. (2001) *Infec. Immun.* 69(5):3510-3515); *Bacillus anthracis* (anthrax): such as *B. anthracis* antigens (optionally detoxified) from A-components (lethal factor (LF) and edema factor (EF)), both of which can share a common B-component known as protective antigen (PA); *Moraxella catarrhalis*: (respiratory) including outer membrane protein antigens (HMW-OMP), C-antigen, and/or LPS; *Yersinia pestis* (plague): such as F1 capsular antigen (Grosveld et al. (2003) *Infec. Immun.* 71 (1):374-383), LPS (Fields et al. (1999) *Infec. Immun.* 67(10):5395), *Yersinia pestis* V antigen (Hill et al. (1997) *Infec. Immun.* 65(11):4476-4482); *Yersinia enterocolitica* (gastrointestinal pathogen): particularly LPS (Xu et al. (2002) *Infec. Immun.* 70(8):4414-4420); *Yersinia pseudotuberculosis*: gastrointestinal pathogen antigens; *Mycobacterium tuberculosis*: such as lipoproteins, LPS, BCG antigens, a fusion protein of antigen 85B (Ag85B) and/or ESAT-6 optionally formulated in cationic lipid vesicles (Olsen et al. (2004) *Infec. Immun.* 72(10):6148-6150), *Mycobacterium tuberculosis* (Mtb) isocitrate dehydrogenase associated antigens (Banerjee et al. (2004) *Proc. Nat'l Acad. Sci USA* 101 (34):12652-12657) and/or MPT51 antigens (Suzuki et al. (2004) *Infec. Immun.* 72(7):3829-3837); *Legionella pneumophila* (Legionnairs' Disease): *L. pneumophila* antigens—optionally derived from cell lines with disrupted asd genes (Harb et al. (1998) *Infec. Immun.* 66(5): 1898-1903; *Rickettsia*: including outer membrane proteins, including the outer membrane protein A and/or B (OmpB) (*Biochim Biophys Acta.* 2004 Nov. 1; 1702(2):145), LPS, and surface protein antigen (SPA) (*J Autoimmun.* 1989 June; 2 Suppl:81); *E. coli*: including antigens from enterotoxigenic *E. coli* (ETEC), enteroaggregative *E. coli* (EAggEC), diffusely adhering *E. coli* (DAEC), enteropathogenic *E. coli* (EPEC), and/or enterohemorrhagic *E. coli* (EHEC); *Vibrio cholerae*: including proteinase antigens, LPS, particularly lipopolysaccharides of *Vibrio cholerae* H, O1 Inaba O-specific polysaccharides, *V. cholera* O139, antigens of IEM108 vaccine (*Infect Immun.* 2003 October; 71(10):5498-504), and/or Zonula occludens toxin (Zot); *Salmonella typhi* (typhoid fever): including capsular polysaccharides preferably conjugates (Vi, i.e. vax-TyVi); *Salmonella typhimurium* (gastroenteritis): antigens derived therefrom are contemplated for microbial and cancer therapies, including angiogenesis inhibition and modulation of flk; *Listeria monocytogenes* (sytemic infections in immunocompromised or elderly people, infections of fetus): antigens derived from *L. monocytogenes* are preferably used as carriers/vectors for intracytoplasmic delivery of conjugates/associated compositions of the present invention; *Porphyromonas gingivalis*: particularly, *P. gingivalis* outer membrane protein (OMP); Tetanus: such as tetanus toxoid (TT) antigens, preferably used as a carrier protein in conjunction/conjugated with the compositions of the present invention; Diphtheria: such as a diphtheria toxoid, preferably $CRM_{197}$, additionally antigens capable of modulating, inhibiting or associated with ADP ribosylation are contemplated for combination/co-administration/conjugation with the compositions of the present invention, the diphtheria toxoids are preferably used as carrier proteins; *Borrelia burgdorferi* (Lyme disease): such as antigens associated with P39 and P13 (an integral membrane protein, (Noppa et al. (2001) *Infec. Immun.* 69(5):3323), VlsE Antigenic Variation Protein (Lawrenz et al. (1999) *J Clin Microbiol.* 37(12):3997); *Haemophilus influenzae* B: such as a saccharide antigen therefrom; *Klebsiella*: such as an OMP, including OMP A, or a polysaccharide optionally conjugated to tetanus toxoid; *Neiserria gonorrhoeae*: including, a Por (or porin) protein, such as PorB (see Zhu et al., Vaccine (2004) 22:660-669), a transferring binding protein, such as ThpA and TbpB (See Price et al., Infection and Immunity (2004) 71(1):277-283), a opacity protein (such as Opa), a reduction-modifiable protein (Rmp), and outer membrane vesicle (OMV) preparations (see Plante et al., J Infectious Disease (2000) 182:848-855), also see e.g. WO99/24578, WO99/36544, WO99/57280, WO02/079243); *Chlamydia pneumoniae*: particularly *C. pneumoniae* protein antigens; *Chlamydia trachomatis*: including antigens derived from serotypes A, B, Ba and C are (agents of trachoma, a cause of blindness), serotypes $L_1$, $L_2$ & $L_3$ (associated with Lymphogranuloma venereum), and serotypes, D-K; *Treponema pallidum* (Syphilis): particularly a TmpA antigen; and *Haemophilus ducreyi* (causing chancroid): including outer membrane protein (DsrA).

Where not specifically referenced, further sequences encoding bacterial antigens of the invention may be capsular antigens, polysaccharide antigens or protein antigens of any of the above. Further bacterial antigens may also include an outer membrane vesicle (OMV) preparation. Additionally, antigens include live, attenuated, split, and/or purified versions of any of the aforementioned bacteria. The bacterial or microbial derived antigens of the present invention may be gram-negative or gram-positive and aerobic or anaerobic.

Additionally, any of the above bacterial-derived saccharides (polysaccharides, LPS, LOS or oligosaccharides) can be conjugated to another agent or antigen, such as a carrier protein (for example $CRM_{197}$). Such conjugation may be direct conjugation effected by reductive amination of carbonyl moieties on the saccharide to amino groups on the protein, as provided in U.S. Pat. No. 5,360,897 and *Can J Biochem Cell Biol.* 1984 May; 62(5):270-5. Alternatively, the saccharides can be conjugated through a linker, such as, with succinamide or other linkages provided in *Bioconjugate Techniques*, 1996 and *CRC, Chemistry of Protein Conjugation and Cross-Linking*, 1993.

Heterologous sequence may also encode one or more viral antigens, for example, Influenza: including whole viral particles (attenuated), split, or subunit comprising hemagglutinin (HA) and/or neuraminidase (NA) surface proteins, the influenza antigens may be derived from chicken embryos or propogated on cell culture, and/or the influenza antigens are derived from influenza type A, B, and/or C, among others; Respiratory syncytial virus (RSV): including the F protein of the A2 strain of RSV (*J Gen Virol.* 2004 November; 85(Pt 11):3229) and/or G glycoprotein; Parainfluenza virus (PIV): including PIV type 1, 2, and 3, preferably containing hemagglutinin, neuraminidase and/or fusion glycoproteins; Poliovirus: including antigens from a family of picornaviridae, preferably poliovirus antigens such as OPV or, preferably IPV; Measles: including split measles virus (MV) antigen optionally combined with the Protollin and or antigens present in MMR vaccine; Mumps: including antigens present in MMR vaccine; Rubella: including antigens present in MMR vaccine as well as other antigens from Togaviridae, including dengue virus; Rabies: such as lyophilized inactivated virus (RabAvert™); Flaviviridae viruses: such as (and antigens derived therefrom) yelow fever virus, Japanese encephalitis virus, dengue virus (types 1, 2, 3, or 4), tick borne encephalitis virus, and West Nile virus; Caliciviridae; antigens therefrom; HIV: including HIV-1 or HIV-2 strain antigens, such as gag (p24gag and p55gag), env (gp160 and gp41), pol, tat, nef, rev vpu, miniproteins, (preferably p55 gag and gp140v delete) and antigens from the isolates $HIV_{IIIb}$, $HIV_{SF2}$, $HIV_{LAV}$, $HIV_{LA1}$, $HIV_{MN}$, HIV-$1_{CM235}$, HIV-$1_{US4}$, HIV-2; simian immunodeficiency virus (SIV) among others; Rotavirus: including VP4, VP5, VP6, VP7, VP8 proteins (*Protein Expr Purif.* 2004 December; 38(2):205) and/or NSP4; Pestivirus: such as antigens from classical porcine fever virus, bovine viral diarrhoea virus, and/or border disease virus; Parvovirus: such as parvovirus B19; Coronavirus: including SARS virus antigens, particularly spike protein or proteases therefrom, as well as antigens included in WO 04/92360; Hepatitis A virus: such as inactivated virus; Hepatitis B virus: such as the surface and/or core antigens (sAg), as well as the presurface sequences, pre-S1 and pre-S2 (formerly called pre-S), as well as combinations of the above, such as sAg/pre-S1, sAg/pre-S2, sAg/pre-S1/pre-S2, and pre-S1/pre-S2, (see, e.g., "HBV Vaccines—*Human Vaccines and Vaccination*, pp. 159-176; and U.S. Pat. Nos. 4,722,840, 5,098,704, 5,324,513; Beames et al., *J. Virol.* (1995) 69:6833-6838, Birnbaum et al., *J. Virol.* (1990) 64:3319-3330; and Zhou et al., *J. Virol.* (1991) 65:5457-5464); Hepatitis C virus: such as E1, E2, E1/E2 (see, Houghton et al., *Hepatology* (1991) 14:381), NS345 polyprotein, NS345-core polyprotein, core, and/or peptides from the nonstructural regions (International Publication Nos. WO 89/04669; WO 90/11089; and WO 90/14436); Delta hepatitis virus (HDV): antigens derived therefrom, particularly δ-antigen from HDV (see, e.g., U.S. Pat. No. 5,378,814); Hepatitis E virus (HEV); antigens derived therefrom; Hepatitis G virus (HGV); antigens derived therefrom; Varcicella zoster virus: antigens derived from varicella zoster virus (VZV) (*J. Gen. Virol.* (1986) 67:1759); Epstein-Barr virus: antigens derived from EBV (Baer et al., *Nature* (1984) 310:207); Cytomegalovirus: CMV antigens, including gB and gH (Cytomegaloviruses (J. K. McDougall, ed., Springer-Verlag 1990) pp. 125-169); Herpes simplex virus: including antigens from HSV-1 or HSV-2 strains and glycoproteins gB, gD and gH (McGeoch et al., *J. Gen. Virol.* (1988) 69:1531 and U.S. Pat. No. 5,171,568);

Human Herpes Virus: antigens derived from other human herpesviruses such as HHV6 and HHV7; and HPV: including antigens associated with or derived from human papillomavirus (HPV), for example, one or more of E1-E7, L1, L2, and fusions thereof, particularly the compositions of the invention may include a virus-like particle (VLP) comprising the L1 major capsid protein, more particular still, the HPV antigens are protective against one or more of HPV serotypes 6, 11, 16 and/or 18.

Further provided are antigens, compostions, methods, and microbes included in *Vaccines*, 4$^{th}$ Edition (Plotkin and Orenstein ed. 2004); *Medical Microbiology* 4$^{th}$ Edition (Murray et al. ed. 2002); *Virology*, 3rd Edition (W. K. Joklik ed. 1988); *Fundamental Virology*, 2nd Edition (B. N. Fields and D. M. Knipe, eds. 1991), which are contemplated in conjunction with the compositions of the present invention.

Additionally, heterologous sequence may encode one or more fungal antigens, including, but not limited to, those described in: U.S. Pat. Nos. 4,229,434 and 4,368,191 for prophylaxis and treatment of trichopytosis caused by *Trichophyton mentagrophytes*; U.S. Pat. Nos. 5,277,904 and 5,284,652 for a broad spectrum dermatophyte vaccine for the prophylaxis of dermatophyte infection in animals, such as guinea pigs, cats, rabbits, horses and lambs, these antigens comprises a suspension of killed *T. equinum, T. mentagrophytes* (var. *granulare*), *M. canis* and/or *M. gypseum* in an effective amount optionally combined with an adjuvant; U.S. Pat. Nos. 5,453,273 and 6,132,733 for a ringworm vaccine comprising an effective amount of a homogenized, formaldehyde-killed fungi, i.e., *Microsporum canis* culture in a carrier; U.S. Pat. No. 5,948,413 involving extracellular and intracellular proteins for pythiosis. Additional antigens identified within antifungal vaccines include Ringvac bovis LTF-130 and Bioveta.

Further, fungal antigens for use herein may be derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album*, var. *discoides*, var. *ochraceum, Trichophyton violaceum*, and/or *Trichophyton faviforme*.

Fungal pathogens for use as antigens or in derivation of antigens in conjunction with the compositions of the present invention comprise *Aspergillus fumigatus, Aspergillus flavus, Aspergillus niger, Aspergillus nidulans, Aspergillus terreus, Aspergillus sydowi, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, and *Saksenaea* spp.

Other fungi from which antigens are derived include *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

Heterologous sequences as described herein may encode one or more tumor or cancer antigens, including but not limited to, a saccharide-containing tumor antigen, such as a glycolipid tumor antigen or a ganglioside tumor antigen. Numerous tumor antigens are known in the art, including: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT, (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma), (e) prostate associated antigens such as PAP, PSA, PSMA, PSH-P1, PSM-P1, PSM-P2, associated with e.g., prostate cancer, (f) immunoglobulin idiotypes (associated with myeloma and B cell lymphomas, for example), and (g) other tumor antigens, such as polypeptide- and saccharide-containing antigens including (i) glycoproteins such as sialyl Tn and sialyl Le$^x$ (associated with, e.g., breast and colorectal cancer) as well as various mucins; glycoproteins may be coupled to a carrier protein (e.g., MUC-1 may be coupled to KLH); (ii) lipopolypeptides (e.g., MUC-1 linked to a lipid moiety); (iii) polysaccharides (e.g., Globo H synthetic hexasaccharide), which may be coupled to a carrier proteins (e.g., to KLH), (iv) gangliosides such as GM2, GM12, GD2, GD3 (associated with, e.g., brain, lung cancer, melanoma), which also may be coupled to carrier proteins (e.g., KLH).

Additional tumor antigens which are known in the art include p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, and the like. These as well as other cellular components are described for example in United States Patent Application 20020007173 and references cited therein.

Additional information on cancer or tumor antigens can be found, for example, in Moingeon P, "Cancer vaccines," Vaccine, 2001, 19:1305-1326; Rosenberg S A, "Progress in human tumor immunology and immunotherapy," Nature, 2001, 411:380-384; Dermine, S. et al, "Cancer Vaccines and Immunotherapy," British Medical Bulletin, 2002, 62, 149-162; Espinoza-Delgado I., "Cancer Vaccines," The Oncologist, 2002, 7(suppl3):20-33; Davis, I. D. et al., "Rational approaches to human cancer immunotherapy," Journal of Leukocyte Biology, 2003, 23: 3-29; Van den Eynde B, et al., "New tumor antigens recognized by T cells," Curr. Opin. Immunol., 1995, 7:674-81; Rosenberg S A, "Cancer vaccines based on the identification of genes encoding cancer regression antigens, Immunol. Today, 1997, 18:175-82; Offringa R et al., "Design and evaluation of antigen-specific vaccination strategies against cancer," Current Opin. Immunol., 2000, 2:576-582; Rosenberg S A, "A new era for cancer immunotherapy based on the genes that encode cancer antigens," Immunity, 1999, 10:281-7; Sahin U et al., "Serological identification of human tumor antigens," Curr. Opin. Immunol., 1997, 9:709-16; Old L J et al., "New paths in human cancer serology," J. Exp. Med., 1998, 187:1163-7; Chaux P, et al., "Identification of MAGE-3 epitopes presented by HLA-DR molecules to CD4(+) T lymphocytes," J. Exp. Med., 1999, 189:767-78; Gold P, et al., "Specific carcinoembryonic antigens of the human digestive system," J. Exp. Med., 1965, 122:467-8; Livingston P O, et al., Carbohydrate vaccines that induce antibodies against cancer: Rationale," Cancer Immunol. Immunother., 1997, 45:1-6; Livingston P O, et al., Carbohydrate vaccines that induce antibodies against cancer: Previous experience and future plans," Cancer Immunol. Immunother., 1997, 45:10-9; Taylor-Papadimitriou J, "Biology, biochemistry and immunology of carcinoma-associated mucins," Immunol. Today, 1997, 18:105-7; Zhao X-J et al., "GD2 oligosaccharide: target for cytotoxic T lymphocytes," J. Exp. Med., 1995, 182:67-74; Theobald M, et al., "Targeting p53 as a general tumor antigen," Proc. Natl. Acad. Sci. USA, 1995, 92:11993-7; Gaudernack G, "T cell responses against mutant ras: a basis for novel cancer vaccines," Immunotechnology, 1996, 2:3-9; WO 91/02062; U.S. Pat. No. 6,015,567; WO 01/08636; WO 96/30514; U.S. Pat. No. 5,846,538; and U.S. Pat. No. 5,869,445.

Formulations

Pharmaceutical compositions comprising the sequences, vectors and particles produced using these molecules described herein are also provided, for example a population of alphavirus replicon particles produced using a helper construct comprising a modified 5' amplification sequence in combination with a pharmaceutically acceptable carrier, diluent, or recipient.

The compositions described herein can include various excipients, adjuvants, carriers, auxiliary substances, modulating agents, and the like. As noted above, compositions of the invention can also contain liquids or excipients, such as water, saline, glycerol, dextrose, ethanol, or the like, singly or in combination, as well as substances such as wetting agents, emulsifying agents, or pH buffering agents. A thorough discussion of pharmaceutically acceptable excipients is available in Gennaro (2000) Remington: The Science and Practice of Pharmacy. 20th ed ISBN: 0683306472.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art.

In certain embodiments, the compositions described herein (e.g., particles) may be preserved either in crude or purified forms, which can also be lyophilized, spray-dried or evaporated, for example as described in detail in U.S. Pat. No. 6,015,686.

As noted above, the formulations described herein may further include or may be administered in conjunction with other immunoregulatory agents. In particular, compositions will usually include an adjuvant. Adjuvants for use with the invention include, but are not limited to, one or more of the following set forth below:

Mineral Containing Compositions

Mineral containing compositions suitable for use as adjuvants in the invention include mineral salts, such as aluminum salts and calcium salts. The invention includes mineral salts such as hydroxides (e.g. oxyhydroxides), phosphates (e.g. hydroxyphosphates, orthophosphates), sulfates, etc. (e.g. see chapters 8 & 9 of Vaccine Design . . . (1995) eds. Powell & Newman. ISBN: 030644867X. Plenum.), or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being preferred. The mineral containing compositions may also be formulated as a particle of metal salt (WO00/23105).

Aluminum salts may be included in vaccines of the invention such that the dose of $Al^{3+}$ is between 0.2 and 1.0 mg per dose.

In one embodiment the aluminum based adjuvant is alum (aluminum potassium sulfate ($AlK(SO_4)_2$)), or an alum derivative, such as that formed in-situ by mixing an antigen in phosphate buffer with alum, followed by titration and precipitation with a base such as ammonium hydroxide or sodium hydroxide.

Another aluminum-based adjuvant for use with the immunogenic compositions described herein is aluminum hydroxide adjuvant ($Al(OH)_3$) or crystalline aluminum oxyhydroxide (AlOOH), which is an excellent adsorbant, having a surface area of approximately 500 $m^2/g$. Alternatively, aluminum phosphate adjuvant ($AlPO_4$) or aluminum hydroxyphosphate, which contains phosphate groups in place of some or all of the hydroxyl groups of aluminum hydroxide adjuvant is provided. Preferred aluminum phosphate adjuvants provided herein are amorphous and soluble in acidic, basic and neutral media.

In another embodiment, the adjuvant comprises both aluminum phosphate and aluminum hydroxide. In a more particular embodiment thereof, the adjuvant has a greater amount of aluminum phosphate than aluminum hydroxide, such as a ratio of 2:1, 3:1, 4:1, 5:1, 6:1, 7:1, 8:1, 9:1 or greater than 9:1, by weight aluminum phosphate to aluminum hydroxide. More particular still, aluminum salts in the vaccine are present at 0.4 to 1.0 mg per vaccine dose, or 0.4 to 0.8 mg per vaccine dose, or 0.5 to 0.7 mg per vaccine dose, or about 0.6 mg per vaccine dose.

Generally, the preferred aluminum-based adjuvant(s), or ratio of multiple aluminum-based adjuvants, such as aluminum phosphate to aluminum hydroxide is selected by optimization of electrostatic attraction between molecules such that the antigen carries an opposite charge as the adjuvant at the desired pH. For example, aluminum phosphate adjuvant (iep=4) adsorbs lysozyme, but not albumin at pH 7.4. Should albumin be the target, aluminum hydroxide adjuvant would be selected (iep 11.4). Alternatively, pretreatment of aluminum hydroxide with phosphate lowers its isoelectric point, making it a preferred adjuvant for more basic antigens.

A. Oil-Emulsions

Oil-emulsion compositions suitable for use as adjuvants include squalene-water emulsions, such as MF59 (5% Squalene, 0.5% Tween 80, and 0.5% Span 85, formulated into submicron particles using a microfluidizer). See WO90/14837. See also, Podda, "The adjuvanted influenza vaccines with novel adjuvants: experience with the MF59-adjuvanted vaccine", Vaccine (2001) 19: 2673-2680; Frey et al., "Comparison of the safety, tolerability, and immunogenicity of a MF59-adjuvanted influenza vaccine and a non-adjuvanted influenza vaccine in non-elderly adults", Vaccine (2003) 21:4234-4237. MF59 is used as the adjuvant in the FLUAD™ influenza virus trivalent subunit vaccine.

Particularly preferred adjuvants for use with the immunogenic compositions described herein are submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v Tween 80™ (polyoxyelthylenesorbitan monooleate), and/or 0.25-1.0% Span 85™ (sorbitan trioleate), and, optionally, N-acetylmuramyl-L-alanyl-D-isogluatminyl-L-alanine-2-(1'-2'-dipalmitoyl-sn-glycero-3-huydroxyphosphoryloxy)-ethylamine (MTP-PE), for example, the submicron oil-in-water emulsion known as "MF59" (International Publication No. WO90/14837; U.S. Pat. Nos. 6,299,884 and 6,451,325, and Ott et al., "MF59—Design and Evaluation of a Safe and Potent Adjuvant for Human Vaccines" in *Vaccine Design: The Subunit and Adjuvant Approach* (Powell, M. F. and Newman, M. J. eds.) Plenum Press, New York, 1995, pp. 277-296). MF59 contains 4-5% w/v Squalene (e.g. 4.3%), 0.25-0.5% w/v Tween 80™, and 0.5% w/v Span 85™ and optionally contains various amounts of MTP-PE, formulated into submicron particles using a microfluidizer such as Model 110Y microfluidizer (Microfluidics, Newton, Mass.). For example, MTP-PE may be present in an amount of about 0-500 µg/dose, more preferably 0-250 µg/dose and most preferably, 0-100 µg/dose. As used herein, the term "MF59-0" refers to the above submicron oil-in-water emulsion lacking MTP-PE, while the term MF59-MTP denotes a formulation that contains MTP-PE. For instance, "MF59-100" contains 100 µg MTP-PE per dose, and so on. MF69, another submicron oil-in-water emulsion for use herein, contains 4.3% w/v squalene, 0.25% w/v Tween 80™, and 0.75% w/v Span 85™ and optionally MTP-PE. Yet another submicron oil-in-water emulsion is MF75, also known as SAF, containing 10% squalene, 0.4% Tween 80™, 5% pluronic-blocked polymer L121; and thr-MDP, also microfluidized into a submicron emulsion. MF75-MTP denotes an MF75 formulation that includes MTP, such as from 100-400 µg MTP-PE per dose.

Submicron oil-in-water emulsions, methods of making the same and immunostimulating agents, such as muramyl peptides, for use in the compositions, are described in detail in International Publication No. WO90/14837 and U.S. Pat. Nos. 6,299,884 and 6,451,325.

Complete Freund's adjuvant (CFA) and incomplete Freund's adjuvant (IFA) may also be used as adjuvants in the invention.

B. Saponin Formulations

Saponin formulations may also be used as adjuvants. Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponins can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs.

Saponin compositions have been purified using High Performance Thin Layer Chromatography (HP-TLC) and Reversed Phase High Performance Liquid Chromatography (RP-HPLC). Specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (see WO96/33739).

Combinations of saponins and cholesterols can be used to form unique particles called Immunostimulating Complexes (ISCOMs). ISCOMs typically also include a phospholipid such as phosphatidylethanolamine or phosphatidylcholine. Any known saponin can be used in ISCOMs. Preferably, the ISCOM includes one or more of Quil A, QHA and QHC. ISCOMs are further described in EP0109942, WO96/11711 and WO96/33739. Optionally, the ISCOMS may be devoid of (an) additional detergent(s). See WO00/07621.

A review of the development of saponin based adjuvants can be found in Barr, et al., "ISCOMs and other saponin based adjuvants", Advanced Drug Delivery Reviews (1998) 32:247-271. See also Sjolander, et al., "Uptake and adjuvant activity of orally delivered saponin and ISCOM vaccines", Advanced Drug Delivery Reviews (1998) 32:321-338.

C. Virosomes and Virus Like Particles (VLPs)

Virosomes and Virus Like Particles (VLPs) can also be used as adjuvants in the invention. These structures generally contain one or more proteins from a virus optionally combined or formulated with a phospholipid. They are generally non-pathogenic, non-replicating and generally do not contain any of the native-viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in WO03/024480, WO03/024481, and Niikura et al., "Chimeric Recombinant Hepatitis E Virus-Like Particles as an Oral Vaccine Vehicle Presenting Foreign Epitopes", Virology (2002) 293:273-280; Lenz et al., "Papillomarivurs-Like Particles Induce Acute Activation of Dendritic Cells", Journal of Immunology (2001) 5246-5355; Pinto, et al., "Cellular Immune Responses to Human Papillomavirus (HPV)-16 L1

Healthy Volunteers Immunized with Recombinant HPV-16 L1 Virus-Like Particles", Journal of Infectious Diseases (2003) 188:327-338; and Gerber et al., "Human Papillomavrisu Virus-Like Particles Are Efficient Oral Immunogens when Coadministered with *Escherichia coli* Heat-Labile Entertoxin Mutant R192G or CpG", Journal of Virology (2001) 75(10):4752-4760. Virosomes are discussed further in, for example, Gluck et al., "New Technology Platforms in the Development of Vaccines for the Future", Vaccine (2002) 20:B10-B16. Immunopotentiating reconstituted influenza virosomes (IRIV) are used as the subunit antigen delivery system in the intranasal trivalent IFLEXAL™ product {Mischler & Metcalfe (2002)*Vaccine* 20 Suppl 5:B17-23} and the INFLUVAC PLUS™ product.

D. Bacterial or Microbial Derivatives

Adjuvants suitable for use in the invention include bacterial or microbial derivatives such as:

(1) Non-Toxic Derivatives of Enterobacterial Lipopolysaccharide (LPS)

Such derivatives include Monophosphoryl lipid A (MPL) and 3-O-deacylated MPL (3dMPL). 3dMPL is a mixture of 3 De-O-acylated monophosphoryl lipid A with 4, 5 or 6 acylated chains. A preferred "small particle" form of 3 De-O-acylated monophosphoryl lipid A is disclosed in EP 0 689 454. Such "small particles" of 3dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives e.g. RC-529. See Johnson et al. (1999) *Bioorg Med Chem Lett* 9:2273-2278.

(2) Lipid A Derivatives

Lipid A derivatives include derivatives of lipid A from *Escherichia coli* such as OM-174. OM-174 is described for example in Meraldi et al., "OM-174, a New Adjuvant with a Potential for Human Use, Induces a Protective Response with Administered with the Synthetic C-Terminal Fragment 242-310 from the circumsporozoite protein of *Plasmodium berghei*", Vaccine (2003) 21:2485-2491; and Pajak, et al., "The Adjuvant OM-174 induces both the migration and maturation of murine dendritic cells in vivo", Vaccine (2003) 21:836-842.

(3) Immunostimulatory Oligonucleotides

Immunostimulatory oligonucleotides suitable for use as adjuvants in the invention include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory.

The CpG's can include nucleotide modifications/analogs such as phosphorothioate modifications and can be double-stranded or single-stranded. Optionally, the guanosine may be replaced with an analog such as 2'-deoxy-7-deazaguanosine. See Kandimalla, et al., "Divergent synthetic nucleotide motif recognition pattern: design and development of potent immunomodulatory oligodeoxyribonucleotide agents with distinct cytokine induction profiles", Nucleic Acids Research (2003) 31(9): 2393-2400; WO02/26757 and WO99/62923 for examples of possible analog substitutions. The adjuvant effect of CpG oligonucleotides is further discussed in Krieg, "CpG motifs: the active ingredient in bacterial extracts?", Nature Medicine (2003) 9(7): 831-835; McCluskie, et al., "Parenteral and mucosal prime-boost immunization strategies in mice with hepatitis B surface antigen and CpG DNA", FEMS Immunology and Medical Microbiology (2002) 32:179-185; WO98/40100; U.S. Pat. No. 6,207,646; U.S. Pat. No. 6,239,116 and U.S. Pat. No. 6,429,199.

The CpG sequence may be directed to TLR9, such as the motif GTCGTT or TTCGTT. See Kandimalla, et al., "Toll-like receptor 9: modulation of recognition and cytokine induction by novel synthetic CpG DNAs", Biochemical Society Transactions (2003) 31 (part 3): 654-658. The CpG sequence may be specific for inducing a Th1 immune response, such as a CpG-A ODN, or it may be more specific for inducing a B cell response, such a CpG-B ODN. CpG-A and CpG-B ODNs are discussed in Blackwell, et al., "CpG-A-Induced Monocyte IFN-gamma-Inducible Protein-10 Production is Regulated by Plasmacytoid Dendritic Cell Derived IFN-alpha", J. Immunol. (2003) 170(8):4061-4068; Krieg, "From A to Z on CpG", TRENDS in Immunology (2002) 23(2): 64-65 and WO01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Kandimalla, et al., "Secondary structures in CpG oligonucleotides affect immunostimulatory activity", BBRC (2003) 306:948-953; Kandimalla, et al., "Toll-like receptor 9: modulation of recognition and cytokine induction by novel synthetic GpG DNAs", Biochemical Society Transactions (2003) 31(part 3):664-658; Bhagat et al., "CpG penta- and hexadeoxyribonucleotides as potent immunomodulatory agents" BBRC (2003) 300:853-861 and WO03/035836.

(4) ADP-Ribosylating Toxins and Detoxified Derivatives Thereof

Bacterial ADP-ribosylating toxins and detoxified derivatives thereof may be used as adjuvants in the invention. Preferably, the protein is derived from *E. coli* (i.e., *E. coli* heat labile enterotoxin "LT), cholera ("CT"), or pertussis ("PT"). The use of detoxified ADP-ribosylating toxins as mucosal adjuvants is described in WO95/17211 and as parenteral adjuvants in WO98/42375. Preferably, the adjuvant is a detoxified LT mutant such as LT-K63, LT-R72, and LTR192G. The use of ADP-ribosylating toxins and detoxified derivatives thereof, particularly LT-K63 and LT-R72, as adjuvants can be found in the following references: Beignon, et al., "The LTR72Mutant of Heat-Labile Enterotoxin of *Escherichia coli* Enahnces the Ability of Peptide Antigens to Elicit CD4+ T Cells and Secrete Gamma Interferon after Coapplication onto Bare Skin", Infection and Immunity (2002) 70(6):3012-3019; Pizza, et al., "Mucosal vaccines: non toxic derivatives of LT and CT as mucosal adjuvants", Vaccine (2001) 19:2534-2541; Pizza, et al., "LTK63 and LTR72, two mucosal adjuvants ready for clinical trials" Int. J. Med. Microbiol (2000) 290(4-5):455-461; Scharton-Kersten et al., "Transcutaneous Immunization with Bacterial ADP-Ribosylating Exotoxins, Subunits and Unrelated Adjuvants", Infection and Immunity (2000) 68(9):5306-5313; Ryan et al., "Mutants of *Escherichia coli* Heat-Labile Toxin Act as Effective Mucosal Adjuvants for Nasal Delivery of an Acellular Pertussis Vaccine: Differential Effects of the Nontoxic AB Complex and Enzyme Activity on Th1 and Th2 Cells" Infection and Immunity (1999) 67(12):6270-6280; Partidos et al., "Heat-labile enterotoxin of *Escherichia coli* and its site-directed mutant LTK63 enhance the proliferative and cytotoxic T-cell responses to intranasally co-immunized synthetic peptides", Immunol. Lett. (1999) 67(3):209-216; Peppoloni et al., "Mutants of the *Escherichia coli* heat-labile enterotoxin as safe and strong adjuvants for intranasal delivery of vaccines", Vaccines (2003) 2(2):285-293; and Pine et al., (2002)

"Intranasal immunization with influenza vaccine and a detoxified mutant of heat labile enterotoxin from *Escherichia coli* (LTK63)" J. Control Release (2002) 85(1-3):263-270. Numerical reference for amino acid substitutions is preferably based on the alignments of the A and B subunits of ADP-ribosylating toxins set forth in Domenighini et al., Mol. Microbiol (1995) 15(6):1165-1167.

F. Bioadhesives and Mucoadhesives

Bioadhesives and mucoadhesives may also be used as adjuvants. Suitable bioadhesives include esterified hyaluronic acid microspheres (Singh et al. (2001) *J. Cont. Rele.* 70:267-276) or mucoadhesives such as cross-linked derivatives of polyacrylic acid, polyvinyl alcohol, polyvinyl pyrollidone, polysaccharides and carboxymethylcellulose. Chitosan and derivatives thereof may also be used as adjuvants. See, e.g. WO99/27960.

G. Microparticles

Microparticles may also be used as adjuvants. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

H. Liposomes

Examples of liposome formulations suitable for use as adjuvants are described in U.S. Pat. No. 6,090,406, U.S. Pat. No. 5,916,588, and EP 0 626 169.

I. Polyoxyethylene Ether and Polyoxyethylene Ester Formulations

Adjuvants suitable for use with the immunogenic compositions described herein include polyoxyethylene ethers and polyoxyethylene esters. WO99/52549. Such formulations further include polyoxyethylene sorbitan ester surfactants in combination with an octoxynol (WO01/21207) as well as polyoxyethylene alkyl ethers or ester surfactants in combination with at least one additional non-ionic surfactant such as an octoxynol (WO01/21152).

Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

J. Polyphosphazene (PCPP)

PCPP formulations are described, for example, in Andrianov et al., "Preparation of hydrogel microspheres by coacervation of aqueous polyphophazene solutions", Biomaterials (1998) 19(1-3):109-115 and Payne et al., "Protein Release from Polyphosphazene Matrices", Adv. Drug. Delivery Review (1998) 31(3):185-196.

K. Muramyl Peptides

Examples of muramyl peptides suitable for use as adjuvants in the invention include N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-isoglutaminyl-1-alanine-2-(1'-2'-dipalmitoyl-sn-glycero-3-hydroxyphosphoryloxy)-ethylamine MTP-PE).

L. Imidazoquinoline Compounds.

Examples of imidazoquinoline compounds suitable for use adjuvants in the invention include Imiquimod and its analogues, described further in Stanley, "Imiquimod and the imidazoquinolines: mechanism of action and therapeutic potential" Clin Exp Dermatol (2002) 27(7):571-577; Jones, "Resiquimod 3M", Curr Opin Investig Drugs (2003) 4(2): 214-218; and U.S. Pat. Nos. 4,689,338, 5,389,640, 5,268,376, 4,929,624, 5,266,575, 5,352,784, 5,494,916, 5,482,936, 5,346,905, 5,395,937, 5,238,944, and 5,525,612.

M. Thiosemicarbazone Compounds

Examples of thiosemicarbazone compounds, as well as methods of formulating, manufacturing, and screening for compounds all suitable for use as adjuvants in the invention include those described in WO04/60308. The thiosemicarbazones are particularly effective in the stimulation of human peripheral blood mononuclear cells for the production of cytokines, such as TNF-●.

N. Tryptanthrin Compounds

Examples of tryptanthrin compounds, as well as methods of formulating, manufacturing, and screening for compounds all suitable for use as adjuvants in the invention include those described in WO04/64759. The tryptanthrin compounds are particularly effective in the stimulation of human peripheral blood mononuclear cells for the production of cytokines, such as TNF-●.

The invention may also comprise combinations of aspects of one or more of the adjuvants identified above. For example, the following adjuvant compositions may be used in the invention:

(1) a saponin and an oil-in-water emulsion (WO99/11241);

(2) a saponin (e.g., QS21)+a non-toxic LPS derivative (e.g. 3dMPL) (see WO94/00153);

(3) a saponin (e.g., QS21)+a non-toxic LPS derivative (e.g. 3dMPL)+a cholesterol;

(4) a saponin (e.g. QS21)+3dMPL+IL-12 (optionally+a sterol) (WO98/57659);

(5) combinations of 3dMPL with, for example, QS21 and/or oil-in-water emulsions (See European patent applications 0835318, 0735898 and 0761231);

(6) SAF, containing 10% Squalane, 0.4% Tween 80, 5% pluronic-block polymer L121, and thr-MDP, either microfluidized into a submicron emulsion or vortexed to generate a larger particle size emulsion.

(7) Ribi™ adjuvant system (RAS), (Ribi Immunochem) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dPML).

(9) one or more mineral salts (such as an aluminum salt)+ an immunostimulatory oligonucleotide (such as a nucleotide sequence including a CpG motif).

O. Human Immunomodulators

Human immunomodulators suitable for use as adjuvants in the invention include cytokines, such as interleukins (e.g. IL-1, IL-2, IL-4, IL-5, IL-6, IL-7, IL-12, etc.), interferons (e.g. interferon-γ), macrophage colony stimulating factor, and tumor necrosis factor.

Aluminum salts and MF59 are preferred adjuvants for use with injectable influenza vaccines. Bacterial toxins and bioadhesives are preferred adjuvants for use with mucosally-delivered vaccines, such as nasal vaccines.

The contents of all of the above cited patents, patent applications and journal articles are incorporated by reference as if set forth fully herein.

Kits

The compositions described herein can also be provided as kits, for example a kit comprising a helper construct or packaging cell line as described herein. One or more of the components may be freeze-dried and/or spray-dried for packaging into the kit. The components may be provided as a single composition or may be provided separately. Furthermore, the components may be reconstituted prior to use such that they are suitable for mucosal administration. The kits described herein may further include additional components such as syringes, reconstitution solutions, instruction manuals, and the like.

The following examples are included to more fully illustrate the present invention. Additionally, these examples provide preferred embodiments of the invention and are not meant to limit the scope thereof. Further, recitation of ranges of values herein are merely intended to serve as a shorthand method of referring individually to each separate value falling within the range, unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Example 1

Preparation of a Modified 5' Amplification Sequence

The 5' region of tRNAasp was aligned with the putative SIN packaging signal and a region of high homology was identified (FIG. 2). In particular, the region defined by nucleotides 1029 to 1050 of the putative SIN packaging signal (described in certain references as nucleotides 945-1076) exhibited greater than 80% homology (18 of 22 nucleotides) to residues 37 to 59 of the tRNAasp amplification sequence.

Using the mfold program (Zucker et al.), the secondary structure of wild type tRNAasp was predicted (FIGS. 4A and 4B). Mutations were introduced into the tRNA structure contained in the helpers tDH-HRcap (capsid gene from SIN HR strain inserted into tDH backbone, see WO 02/099035) and tDH-VutrSGly (WO 02/099035; Perri et al. (2003) J Virol. 77(19):10394-403). Specifically, the mutations were introduced within the region of homology to the SIN packaging signal by site directed mutagenesis to change the primary nucleotide sequence but maintain the overall secondary structure similar to that of wild-type tRNA$_{Asp}$. The modified 5' sequences are shown in FIG. 3 and the helper constructs containing these modified sequences were called tMOD-HRcap and tMOD-VutrSGly. The modified 5' amplification sequences are shown in FIG. 3.

Example 2

Packaging of Alphavirus Replicon Particles Using Structural Cassettes with Modified 5' Amplification Sequences The modified 5' amplification sequence designated mod #1 was produced as described in Example 1 and was used to package a GFP-expressing replicon vector, essentially as described in Gardner et al. (2000) *J. Virol* 74(24): 11849-11857.

To test the functionality of the modified helpers, the plasmid SINCR-GFP encoding the replicon, the helpers both with wild-type tRNA or modified sequences were linearized with the single restriction enzyme PmeI and RNA was transcribed in vitro. The replicon RNA was co-transfected together with defective helper RNAs encoding SIN capsid and glycoprotein from constructs as described in table 1.

Transfected cells were incubated at 34° C. for 24 hr, at which time the culture supernatants were collected, clarified by centrifugation, serially diluted, and used to infect naïve BHK-21 cells for approximately 14 hr. Using flow cytometry analysis(FACS) the particles titers were determined. Results are shown in Table 1.

TABLE 1

| Helper RNAs | | |
|---|---|---|
| CAPSID | ENVELOPE | Titer IU/ml |
| tDH-HRcap | tDH-VutrSGly | 7.75E+07 |
| tMOD-HRcap | tDH-VutrSGly | 5.79E+07 |
| tDH-HRcap | tMOD-VutrSGly | 6.17E+06 |
| tMOD-HRcap | tMOD-VutrSGly | 5.15E+07 |

The particles were also tested for their infectivity and ability to produce new particles upon infection of naïve cells, a measure of defective helper co-packaging. At high MOI infection, particles produced using constructs comprising the modified amplification sequences infected naïve cells much more efficiently than particles produced using constructs comprising the unmodified amplification sequences. Thus, particles produced using structural cassettes comprising modified 5' amplification sequences contained fewer abortive particles.

Furthermore, as shown in FIGS. 4A and 4B, particles produced using structural cassettes comprising modified 5' amplification sequences have at least 10-fold fewer co-packaged particles as compared to particles generated using unmodified amplification sequences.

Finally, the infectivity of particles produced with at least one helper containing the tRNA structure was compared to the infectivity of particles prepared with helpers containing the modified 5'sequence. Naïve cells were infected at various MOI (0.5, 1, 5, and 10) for 45 min. at 37° C. The cells were then washed and incubated in media overnight. The number of infected cells were evaluated by FACS 16 hr post-infection.

As it is shown in FIG. 6, the number of cells infected with particles prepared with the modified helpers increases as the MOI increases, while the number of cells infected with particles derived from helpers with one tRNA plateaus at the relatively low MOI=1. This result suggests that particle preparations derived from helpers with tRNA have a high number of abortive particles competing to infect cells, therefore the measurable infectivity (e.g. the percentage of GFP positive cells) plateaus early. In contrast, particles derived with the modified helpers have a reduced number of abortive particles and the number of cells infected increases over a range of M.O.I.s.

Thus, using structural helper constructs comprising modified amplification sequences that are defective packaging signals significantly reduces co-packaging while efficiently packaging replicon particles.

Although preferred embodiments of the subject invention have been described in some detail, it is understood that obvious variations can be made without departing from the spirit and the scope of the invention.

What is claimed is:

1. An isolated polynucleotide comprising a 5' modified amplification sequence, wherein the modified sequence provides a recognition site for synthesis of positive strand alphavirus RNA but does not provide a recognition site for RNA packaging in animal cells, and wherein:
   (a) the modified amplification sequence is selected from the group consisting of the nucleotide sequence as set forth in SEQ ID NO: 4-15 and 16, or
   (b) the modified amplification sequence is a full length RNA transcript corresponding to the nucleotide sequence as set forth in SEQ ID NO: 4-15 or 16.

2. The isolated polynucleotide of claim 1, wherein the polynucleotide is RNA.

3. The polynucleotide of claim 1, wherein the 5' modified amplification sequence is derived from a sequence selected from the group consisting of a native alphavirus 5' sequence, a non-native DI alphavirus 5' sequence, a non-alphavirus viral sequence and a cellular RNA sequence.

4. An RNA vector construct comprising the 5' amplification sequence of claim 1.

5. The vector construct of claim 4, further comprising a nucleic acid sequence encoding an alphavirus junction region promoter; a nucleic acid sequence encoding one or more alphavirus structural proteins; and an RNA polymerase recognition sequence.

6. The vector construct of claim 5, further comprising a nucleic acid sequence encoding a selectable marker.

7. The vector construct of claim 5, wherein the vector does not encode all biologically active alphavirus nonstructural proteins.

8. The vector construct of claim 5, where the alphavirus structural proteins are glycoproteins E2 and E1.

9. The vector construct of claim 5, wherein the alphavirus structural protein is a capsid protein.

10. The vector construct of claim 4, wherein the sequences are derived from more than one alphavirus.

11. An alphavirus vector construct, comprising a 5' promoter operably linked to a nucleic acid molecule, wherein said nucleic acid molecule is complementary DNA to the RNA vector of claim 4.

12. The alphavirus vector construct of claim 11, further comprising a 3' sequence that controls transcription termination.

13. The alphavirus vector construct of claim 12, wherein the 5' promoter is a eukaryotic promoter.

14. The alphavirus vector construct of claim 12, wherein the 5' promoter is a prokaryotic promoter.

15. An isolated cell comprising the RNA vector construct of claim 4.

16. An alphavirus packaging cell line, comprising a host cell and the RNA vector construct of claim 4.

17. An alphavirus-permissive helper cell for producing an infectious, defective alphavirus particle, said helper cell comprising:
   an alphavirus replicon vector; and
   one or more separate helper vector constructs encoding the alphavirus structural protein(s) absent from the replicon vector, wherein at least one of said separate helper constructs comprise the 5' modified amplification sequence of claim 1 and further wherein the combined expression of the replicon vector and the separate helper vectors produces an assembled alphavirus particle which comprises one or more heterologous sequence(s), is able to infect a cell, and is unable to complete viral replication.

18. The helper cell of claim 17, comprising two separate helper constructs, wherein a first helper construct encodes an alphavirus capsid protein and a second helper construct encodes alphavirus glycoproteins.

19. The helper cell of claim 17, wherein all of the one or more separate helper constructs comprise a 5' modified amplification sequence.

20. The helper cell of claim 17, wherein said helper cell is transfected with the alphavirus replicon vectors and the one or more separate helper constructs.

* * * * *

SEQUENCE LISTING

```
<160> NUMBER OF SEQ ID NOS: 16

<210> SEQ ID NO 1
<211> LENGTH: 66
<212> TYPE: DNA
<213> ORGANISM: Artificial Sequence
<220> FEATURE:
<223> OTHER INFORMATION: Synthetic Construct

<400> SEQUENCE: 1
cttcttgcta tgcaaagtta ctgacacagt aaaaggagaa cgggtatcgt tccctgtgtg     60
cacgta                                                                66

<210> SEQ ID NO 2
<211> LENGTH: 68
<212> TYPE: DNA
<213> ORGANISM: Artificial Sequence
<220> FEATURE:
<223> OTHER INFORMATION: Synthetic Construct

<400> SEQUENCE: 2
atggatatag tggtgagtat ccccgcctgt cacgcgggag accggggttc ggttccccga     60
cggggagc                                                              68

<210> SEQ ID NO 3
<211> LENGTH: 36
<212> TYPE: DNA
<213> ORGANISM: Artificial Sequence
<220> FEATURE:
<223> OTHER INFORMATION: Synthetic Construct

<400> SEQUENCE: 3
tttgagtccg taggagacgg gtcgttcgtt cccggg                               36

<210> SEQ ID NO 4
<211> LENGTH: 68
<212> TYPE: DNA
<213> ORGANISM: Artificial Sequence
<220> FEATURE:
<223> OTHER INFORMATION: Synthetic Construct

<400> SEQUENCE: 4
atggatatag tggtgagtat ccccgcctgt cacgccccag cgacgggttg tcgtcgggga     60
cggggagc                                                              68

<210> SEQ ID NO 5
<211> LENGTH: 68
<212> TYPE: DNA
<213> ORGANISM: Artificial Sequence
<220> FEATURE:
<223> OTHER INFORMATION: Synthetic Construct
```

```
<400> SEQUENCE: 5
atggatatag tggtgagtat ccccgcctgt cacgccgcag gctggggttc agctcgcgga    60
cggggagc                                                            68

<210> SEQ ID NO 6
<211> LENGTH: 68
<212> TYPE: DNA
<213> ORGANISM: Artificial Sequence
<220> FEATURE:
<223> OTHER INFORMATION: Synthetic Construct

<400> SEQUENCE: 6
atggatatag tggtgagtat ccccgcctgt cacgcgcgag gtgcggttg cactccgcga    60 cggggagc                                                            68

<210> SEQ ID NO 7
<211> LENGTH: 68
<212> TYPE: DNA
<213> ORGANISM: Artificial Sequence
<220> FEATURE:
<223> OTHER INFORMATION: Synthetic Construct

<400> SEQUENCE: 7
atggatatag tggtgagtat ccccgcctgt cacgccggag cagcggttg ctgtcccgga    60 cggggagc                                                            68

<210> SEQ ID NO 8
<211> LENGTH: 68
<212> TYPE: DNA
<213> ORGANISM: Artificial Sequence
<220> FEATURE:
<223> OTHER INFORMATION: Synthetic Construct

<400> SEQUENCE: 8
atggatatag tggtgagtat ccccgcctgt cacgcggcag gtcggggttc gactcgccga    60
cggggagc                                                            68

<210> SEQ ID NO 9
<211> LENGTH: 68
<212> TYPE: DNA
<213> ORGANISM: Artificial Sequence
<220> FEATURE:
<223> OTHER INFORMATION: Synthetic Construct

<400> SEQUENCE: 9
atggatatag tggtgagtat ccccgcctgt cacgcccgag gctggggttc agctccggga    60
cggggagc                                                            68

<210> SEQ ID NO 10
<211> LENGTH: 68
<212> TYPE: DNA
<213> ORGANISM: Artificial Sequence
<220> FEATURE:
<223> OTHER INFORMATION: Synthetic Construct

<400> SEQUENCE: 10
atggatatag tggtgagtat ccccgcctgt cacgcccag cctggggttc aggtcgggga     60
cggggagc                                                            68

<210> SEQ ID NO 11
<211> LENGTH: 68
```

-continued

<212> TYPE: DNA
<213> ORGANISM: Artificial Sequence
<220> FEATURE:
<223> OTHER INFORMATION: Synthetic Construct

<400> SEQUENCE: 11
atggatatag tggtgagtat ccccgcctgt cacgccccag ggacgggttg tcctcgggga    60
cggggagc                                                            68

<210> SEQ ID NO 12
<211> LENGTH: 68
<212> TYPE: DNA
<213> ORGANISM: Artificial Sequence
<220> FEATURE:
<223> OTHER INFORMATION: Synthetic Construct

<400> SEQUENCE: 12
atggatatag tggtgagtat ccccgcctgt cacgccccag caggggttc ctgtcgggga    60 cggggagc                                                            68

<210> SEQ ID NO 13
<211> LENGTH: 68
<212> TYPE: DNA
<213> ORGANISM: Artificial Sequence
<220> FEATURE:
<223> OTHER INFORMATION: Synthetic Construct

<400> SEQUENCE: 13
atggatatag tggtgagtat ccccgcctgt cacgccccag ccaggggttc tggtcgggga    60
cggggagc                                                            68

<210> SEQ ID NO 14
<211> LENGTH: 68
<212> TYPE: DNA
<213> ORGANISM: Artificial Sequence
<220> FEATURE:
<223> OTHER INFORMATION: Synthetic Construct

<400> SEQUENCE: 14
atggatatag tggtgagtat ccccgcctgt cacgccccag ggtcgggttg acctcgggga    60
cggggagc                                                            68

<210> SEQ ID NO 15
<211> LENGTH: 68
<212> TYPE: DNA
<213> ORGANISM: Artificial Sequence
<220> FEATURE:
<223> OTHER INFORMATION: Synthetic Construct

<400> SEQUENCE: 15
atggatatag tggtgagtat ccccgcctgt cacgccccag cgtcgggttg acgtcgggga    60
cggggagc                                                            68

<210> SEQ ID NO 16
<211> LENGTH: 68
<212> TYPE: DNA
<213> ORGANISM: Artificial Sequence
<220> FEATURE:
<223> OTHER INFORMATION: Synthetic Construct

```
<400> SEQUENCE: 16
atggatatag tggtgagtat ccccgcctgt cacgcccag gacggggttc gtctcgggga      60
cggggagc                                                              68
```